US011851675B2

(12) United States Patent
Lee et al.

(10) Patent No.: US 11,851,675 B2
(45) Date of Patent: Dec. 26, 2023

(54) METHODS AND DEVICES FOR THE GENERATION OF OOCYTES WITH IMPROVED OOCYTE QUALITY FOR IN VITRO FERTILIZATION PROCEDURES USING NON-INVASIVE CELLULAR TRANSFER

(71) Applicant: The Chinese University of Hong Kong, Hong Kong (CN)

(72) Inventors: Tin Lap Lee, Hong Kong (CN); Tin Chiu Li, Hong Kong (CN); Yiu Leung Chan, Hong Kong (CN); Wing Tung Lee, Hong Kong (CN); Kin Wing Judy Ng, Hong Kong (CN); Ting Hei Thomas Chan, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 44 days.

(21) Appl. No.: 17/158,705

(22) Filed: Jan. 26, 2021

(65) Prior Publication Data

US 2021/0238545 A1    Aug. 5, 2021

Related U.S. Application Data

(60) Provisional application No. 62/967,672, filed on Jan. 30, 2020.

(51) Int. Cl.
*C12N 5/075* (2010.01)
*C12M 3/06* (2006.01)
*C12M 1/00* (2006.01)

(52) U.S. Cl.
CPC ............ *C12N 5/0609* (2013.01); *C12M 23/16* (2013.01); *C12M 29/26* (2013.01); *C12N 2502/11* (2013.01); *C12N 2502/1382* (2013.01)

(58) Field of Classification Search
None
See application file for complete search history.

(56) References Cited

FOREIGN PATENT DOCUMENTS

WO    WO-2007/075796 A2    7/2007
WO    WO-2007/075796 A3    7/2007

OTHER PUBLICATIONS

Desai et al. Three-dimensional in vitro follicle growth: overview of culture models, biomaterials, design parameters and future directions. Reproductive Biology and Endocrinology (2010) 8:119, 1-12. (Year: 2010).*
Xia et al. Mesenchymal Stem Cells Facilitate In Vitro Development of Human Preantral Follicle. Reproductive Sciences (2015) 22:11, 1367-1376. (Year: 2015).*
European Search Report dated Jul. 1, 2021 in European Application No. 21153844.2.
Kloc, M. et al., "Exogenous Molecule and Organelle Delivery in Oogenesis," *Oocytes*, Maternal Information and Functions (Results and Problems in Cell Differentiation 63), 2017, pp. 3-16, Springer International Publishing.
Gerdes, H.-H. et al., "Tunneling nanotubes: A new route for the exchange of components between animal cells," *FEBS Letters*, 2007, 581(11):2194-2201, Elsevier B.V.
Gerdes, H.-H. et al., "Intercellular transfer mediated by tunneling nanotubes," Current Opinion in Cell Biology, 2008, 20(4):470-475, Elsevier Ltd.
Plotnikov, E.Y. et al., "Intercellular Transfer of Mitochondria," *Biochemistry (Moscow)*, 2015, 80(5):542-548, Pleiades Publishing.
Vignais, M.-L. et al., "Cell Connections by Tunneling Nanotubes: Effects of Mitochondrial Trafficking on Targert Cell Metabolism, Homeostasis, and Response to Therapy," Stem Cells International, 2017, 2017:1-14.
Jie, H. et al., "In vitro rescue immature oocytes—a literature review," Human Fertility, 2021, pp. 1-20, Taylor & Francis Group.
Sisakhtnezhad, S. et al., "Emerging physiological and pathological implications of tunneling nanotubes formation between cells," European Journal of Cell Biology, 2015, 94(10):429-443, Elsevier GmbH.
Lin, T. "Microfabricated Platform for the Study of Tunneling Nanotubes," UC Irvine Electronic Theses and Dissertations, 2015, pp. 1-85.
Wada, K.-I. et al., "Quantitative control of mitochondria transfer between live single cells using a microfluidic device," Biology Open, 2017, 6:1960-1965, The Company of Biologists Ltd.
Asgharzadeh, S. et al., "The effect of mesenchymal stem cells as co-culture in in vitro nuvlear maturation of ovine oocytes", Animal Science Papers and Reports, 2015, 33(3):223-231, Institute of Genetics and Animal Breeding, Jastrzębiec, Poland.
Craven, L. et al., "Pronuclear transfer in human embryos to prevent transmission of mitochondrial DNA disease", Nature, May 6, 2010, 465:82-87, Macmillan Publishers Limited.
Engelstad, K. et al., "Attitudes toward prevention of mtDNA-related diseases through oocyte mitochondrial replacement therapy", Human Reproduction, 2016, 31(5):1058-1065.
Ling, B. et al., "Effect of conditioned medium of mesenchymal stem cells on the in vitro maturation and subsequent development of mouse oocyte", Brazilian Journal of Medical and Biological Research, 2008, 41:978-985.

(Continued)

*Primary Examiner* — Allison M Fox
*Assistant Examiner* — Alyssa G Weston
(74) *Attorney, Agent, or Firm* — Saliwanchik, Lloyd & Eisenschenk

(57) ABSTRACT

The subject invention pertains to methods and devices for generating mature oocytes from immature oocytes and improving oocyte quality for improved success of assistant reproductive technology (ART). The methods include the use of tunneling nanotube-forming cells and oocytes, wherein the tunneling nanotube-forming cells transfer autologous genomic materials, biomolecules and cellular components to the oocytes. The devices of the invention include microfluidic device to improve the efficiency of the transfer of biomolecules and cellular components between tunneling nanotube-forming cells and oocytes.

10 Claims, 10 Drawing Sheets

(56) References Cited

OTHER PUBLICATIONS

Rajabi, Z. et al., "Mouse preantral follicle growth in 3D co-culture system using human menstrual blood mesenchymal stem cell", Reproductive Biology, 2018, 18:122-131, Society for Biology of Reproduction & the Institute of Animal Reproduction and Food Research of Polish Academy of Sciences in Olsztyn.
Wang, Z.B. et al., "Transfer of autologous mitochondria from adipose tissue-derived stem cells rescues oocyte quality and infertility in aged mice", AGING, 2017, 9(12):2480-2488.
Woods, D.C. et al., "Autologous Germline Mitochondrial Energy Transfer (AUGMENT) in Human Assisted Reproduction", Seminars in Reproductive Medicine, Nov. 2015, 33(6):410-421.
Substantive Examination Report dated Jun. 9, 2023 in European Application No. 21 153 844.2.
Tachibana, M., et al., "Mitochondrial gene replacement in primate offspring and embryonic stem cells," Nature, 2009, 461:367-372.
Chappel, S., "The Role of Mitochondria from Mature Oocyte to Viable Blastocyst," Obstetrics and Gynecology International, 2013, 2013:1-11.

* cited by examiner

METHODS AND DEVICES FOR THE GENERATION OF OOCYTES WITH IMPROVED OOCYTE QUALITY FOR IN VITRO FERTILIZATION PROCEDURES USING NON-INVASIVE CELLULAR TRANSFER

CROSS-REFERENCE TO RELATED APPLICATION

This application claims the benefit of U.S. Patent Application Ser. No. 62/967,672, filed Jan. 30, 2020, which is hereby incorporated by reference in its entirety including any tables, figures, or drawings.

BACKGROUND OF THE INVENTION

In vitro fertilization (IVF) is a technique in assisted reproductive technology used to improve fertility. Mature oocytes and sperms are collected from a donor and oocytes are fertilized by the sperm in a lab. The fertilized egg is then implanted back to the donor's uterus. Collection of oocytes in human requires controlled ovarian hyperstimulation and transvaginal oocyte retrieval. Controlled ovarian hyperstimulation mainly involves injection of gonadotropin, such as follicle-stimulating hormone, followed by human chorionic gonadotropin (hCG) injection 36 hours before oocyte retrieval. The injection is often supplemented with gonadotropin agonist or antagonist, depending on various protocols. In transvaginal oocyte retrieval, a needle is inserted through the vaginal wall into the ovarian follicle under ultrasound guidance. A suction device that is attached to the needle collects the follicular fluid and oocyte. The mature oocytes collected are then used in IVF treatment and fertilization. These procedures are required to obtain a higher number of fertilizable eggs for IVF and implantation. Due to low pregnancy rates in IVF, more than two embryos are often transferred in a single implantation. The excess embryos in IVF can also be cryo-preserved for a second implantation attempt.

In current practice, in vivo matured oocytes are used in IVF practice only, while immature oocytes are discarded in most clinics due to their low fertilization potential. This practice is less significant to young women who receive IVF treatment, because a higher number of mature oocytes are retrieved in a single round of controlled ovarian hyperstimulation. However, when women at advanced maternal age, which is defined as 35 years old or above, receive IVF treatment, the number of mature oocytes collected can be significantly decreased, lowering the chances of successful pregnancy after IVF treatment. Some IVF procedures make use of in vitro maturation (IVM) as an alternative treatment, but low success rate inhibits it from being a conventional procedure. In vitro maturation is a clinical procedure that treats immature germinal vesicle (GV) stage oocytes and meiosis I (MI) stage oocytes to develop into mature MII stage oocytes. Despite recent advances in IVM, the fertilization potential of IVM-matured oocytes remains low. Therefore, it would be desirable to develop an improved in vitro maturation method to utilize GV and MI oocytes.

Replenishing the loss of cytoplasmic materials in aged cells could reverse the effect of aging. In fact, reduced expression of certain biomolecules such as RNA and proteins, has been reported in aged oocytes. Other than biomolecules, the reduction of cellular component number and function has also contributed to adverse reproductive outcomes in aged oocytes. For example, the mitochondrion is the "powerhouse" of the cell and is a key determinant of successful fertilization of oocytes. It generates 90% of cellular energy in the form of ATP. Mitochondria are also important in other functions such as maintaining ion homeostasis and apoptosis. The energy generation capacity of mitochondria is crucial in oocyte maturation and successful fertilization, as some major events including chromosome separation and zygotic genome activation are energy dependent. As a result, good quality oocytes contain optimal mitochondrial numbers and sufficient levels of ATP. Aging is a risk factor for infertility due to declined mitochondrial function. Some studies link increased oxidative stress to maternal age, and oxidative stress results in mitochondrial dysfunction. Oxidative stress is often associated with mutations within the mitochondrial genome, which is much more susceptible to damage due to the lack of histones. As such, mitochondrial function is often compromised in oocytes of advanced maternal age. Reduced mitochondrial function in oocytes can result in meiotic arrest and aneuploidy, which will lead to failure to develop a successful pregnancy.

Therefore, the mitochondrion is the primary target of improving oocyte quality in assisted reproductive technology. Latest methods include pronuclear transfer and maternal spindle transfer. Both procedures require a donor oocyte and could cause mitochondrial genome heteroplasmy. Isolating oogonial stem cell (OSC)-derived compositions, such as nuclear free cytoplasm or isolated mitochondria, followed by manual injection of such materials into an oocyte was also described. However, the existence of OSC is still a topic of debate. Therefore, an autologous replenishment method that features an oocyte-free, non-invasive nature and the use of a proven cell source is urgently needed to improve oocyte quality. The instant invention provides a non-invasive method to transfer mitochondria from adult stem cells to oocyte through tunneling nanotubes.

BRIEF SUMMARY OF THE INVENTION

The present invention describes a novel technique for improving oocyte quality in vitro, which novel technique greatly improves multiple pregnancy outcomes such as maturation rate, fertilization rate and pregnancy rate. The novel technique comprises non-invasive transfer of biomolecules and cellular components from tunneling nanotube-forming cells to an immature or mature oocyte through tunneling nanotubes.

The present invention relates to a method of maturing an oocyte in vitro, comprising incubating an immature oocyte in oocyte maturation medium with tunneling nanotube-forming cells using unique culture methods.

In some embodiments, the culture methods comprise using culture medium that comprises extracellular matrices.

In some embodiments, the methods of the invention enable the transfer of biomolecules and cellular components from a cell source to an oocyte through tunneling nanotubes between both cells, leading to increased biomolecules and mitochondrial content in the oocyte.

In specific embodiments, the methods of the invention comprise overexpressing biomolecules encoded by the Kinesin-1 heavy chain gene (kif5b) in tunneling nanotube-forming cells to increase the number and quality of tunneling nanotubes formed between a cell source and an oocyte for efficient transfer of biomolecules and cellular components.

In some embodiments, the culture methods of the invention comprise culturing an oocyte in a hanging drop with a certain concentration of tunneling nanotube-forming cells.

In further embodiments, the invention provides microfluidic devices that enable an alternative culture method that enables maximum biomolecule and cellular component transfer between donor cells and oocytes.

In some embodiments, the invention provides a microfluidic device made of Polydimethylsiloxane (PDMS) in which device an oocyte is cultured with tunneling nanotube-forming cells. In specific embodiments, the microfluidic device of the invention maximizes tunneling nanotube formation between cells by bringing the tunneling nanotube-forming cells and the oocyte in close proximity. Advantageously, the device of the invention enables the oocyte and the tunneling nanotube-forming cells to be accurately positioned for maximal biomolecule and cellular component transfer by controlling the input flow rate.

The invention also provides a method and device for sorting oocytes from tunneling nanotube-forming cells separately by size and cellular properties. Furthermore, the invention provides methods for in vitro maturation that allows the culture and exposure to tunneling nanotube-forming cells of multiple oocytes in one device and provides methods for the improvement of oocyte quality through the use of tunneling nanotube-forming cells in a microfluidic device.

DETAILED DISCLOSURE OF THE INVENTION

Definitions

Oocytes

Figure 1:
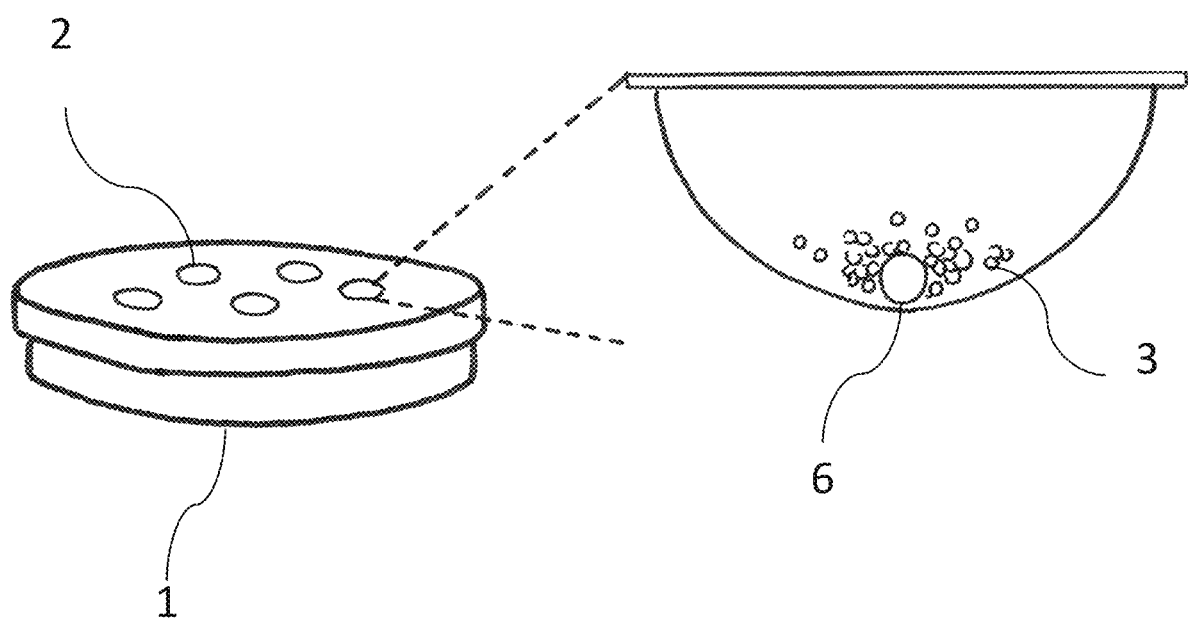
FIG. 1 shows a graph of the hanging drop setup, including the hanging drop inverted on a petri dish, and cross-sectional view of a hanging drop culture comprising about 20 μL medium with an oocyte (6) and tunneling nanotube-forming cells (3).

Oocyte refers to the female germ cell involved in reproduction. Primary oocytes are arrested at the diplotene stage of meiotic prophase I in the fetal stage. After puberty, a surge of luteinizing hormone stimulates the resumption of meiosis. During each menstrual cycle, an oocyte undergoes maturation. The extrusion of a first polar body symbolizes the maturation of an oocyte, which is ready for fertilization.

Immature oocytes used in embodiments of the invention are oocytes that are in the stage of development, including but not limited to, germinal vesicle (GV) stage oocytes, meiosis I (MI) stage oocytes and follicles. In clinical in vitro fertilization (IVF) treatment, immature oocytes may be retrieved along with mature oocytes during controlled ovarian hyperstimulation (COS) and transvaginal oocyte retrieval. Oocytes can also be retrieved from a female who has not received controlled ovarian hyperstimulation.

In humans, the protocol for COS varies between patients, medical providers and clinics, but usually includes but is not limited to, administration of exogenous gonadotropin and/or cotreatment with gonadotropin-releasing hormone (GnRH) agonist or antagonist. The method, duration and dosage of gonadotropin, GnRH agonist and GnRH antagonist are not determining factors in the invention, and are well documented in prior art. Gonadotropin used in COS includes, but is not limited to, human menopausal gonadotropin (hMG), a urinary product with follicle-stimulating hormone (FSH) or luteinizing hormone (LH) activity, purified FSH (p-FSH) or highly purified FSH (hp-FSH), or various recombinant FSH (rFSH) and LH (rFSH/rLH) preparations. At the end of an IVF cycle, human chorionic gonadotropin (hCG) or GnRH agonist or other alternatives may be administered at a certain time interval before oocyte retrieval. Oocytes collected in COS can be used in the embodiments of the instant invention.

Biomolecules and Cellular Components

Biomolecules and cellular components refer to molecules and ions present in a cell and living organism. Biomolecules and cellular components include nucleic acids, proteins, phospholipids, carbohydrate, ions, fluids or cellular components consisting of more than one type of biomolecule. For example, a mitochondrion contains biomolecules including, but not limited to, mitochondrial DNA, RNA, phospholipid membrane, mitochondrial proteins and carbohydrates. Biomolecules and cellular components can be endogenously synthesized by the cell or exogenously introduced from an external source; thus, can be naturally existing or modified. External sources include, but are not limited to, culture medium supplements, transfection and endocytosis.

In some embodiments, biomolecules and organelles are transferred from one cell to another. These biomolecules and organelles include, but not limited to, nucleic acids, proteins and mitochondria. They can be transferred through mechanisms including, but not limited to, tunneling nanotubes. The biomolecules and organelles may or may not exert a change to the recipient cell.

Tunneling Nanotube-Forming Cells

Tunneling nanotube-forming cells refer to a cell type that is able to transfer mitochondria, biomolecules and cellular components including, but not limited to, peptides and hormones to another cell. Tunneling nanotube is a structure composed of microtubules and microfilaments that protrudes from one cell to another cell. The cells being connected by a tunneling nanotube may not be of the same type. Tunneling nanotube-forming cells include, but are not limited to, mammalian adult stem cells, induced pluripotent stem cells, and menstrual blood derived cells.

Adult Stem Cells

Adult stem cells refer to undifferentiated cells found in mammals that have the potential to differentiate into different cell types while being able to self-renew. Examples include hematopoietic stem cells, mesenchymal stem cells, neural stem cells, epithelial stem cells, adipose stem cells, and skin stem cells. Adult stem cells are mostly in a quiescent state under normal physiological conditions. Glycolysis metabolism is the key energy production pathway in adult stem cells, thus protecting the cells from reactive oxygen species (ROS) and damage to mitochondria.

Induced Pluripotent Stem Cells

Induced pluripotent stem cells refer to a type of pluripotent stem cells that are reprogrammed from somatic cells through inducing genes or factors. Examples include genomic integration of one or more Yamanaka factors, including, but not limited to, Oct4, Sox2, Klf4 and c-Myc.

Menstrual Blood Derived Cells

Menstrual blood derived cells refer to a cell population isolated from menstrual blood of humans. These cells may be extracted through adherence to a culture plate, and further selected by fluorescence activated cell sorting. Red blood cell lysis may be done after collection of menstrual blood. Density gradient centrifugation can be used to collect the cell population capable of forming tunneling nanotubes.

Oocyte Treatment Prior to Culture

Immature oocyte undergo treatment prior to culture. Some immature oocytes are surrounded by cumulus, which is also known as cumulus-oocyte-complexes. For example, oocytes can be denuded or isolated from other cell components by using hyaluronidase in phosphate buffered saline or culture medium. Mechanical stripping can also be used to facilitate denuding.

Hanging Drop Culture

Hanging drop culture refers to a 3D hanging drop culture that comprises a drop of culture medium with cells or tissue suspended from an inverted surface.

Small-Scale Culture System

Small-scale culture system refers to a miniature-volume culture system with less than 20 µL of internal total volume and medium.

Microfluidic Device

Microfluidic device refers to a sub-millimeter scale device that provides precise fluid manipulation and a controlled environment for cell culture and growth. Cells inside the microfluidic device are less affected by the external environment and would have a lower batch to batch variation. Furthermore, due to its sub-millimeter scale, a microfluidic device minimizes the cell numbers to be used in cell-cell contact settings. The microfluidic device of the instant invention is a specific sub-millimeter device characterized by a specific arrangement of microchannels that is suited for maximizing cell-cell contacts between tunneling nanotube-forming cells and oocytes.

The instant invention provides methods and devices for the generation of fertilization-competent oocytes from immature and mature oocytes using non-invasive techniques.

The invention further provides methods and devices for maturing immature oocytes in vitro. Advantageously, the methods and devices of the invention allow non-invasive transfer of biomolecules and cellular components including, but not limited to, whole mitochondria to immature and mature oocytes and preserve oocyte quality and functionality by inhibiting oocyte demise often associated with conventional microinjection and electrofusion methods.

In some embodiments, the methods of the instant invention comprise transferring biomolecules including, but not limited to, nucleic acids, proteins, phospholipids, carbohydrate, ions, and fluids to oocytes using non-traumatic biomolecule transfer means. The biomolecules useful in the instant invention can be endogenously synthesized by a cell or exogenously introduced from an external source.

In some embodiments, the methods of the instant invention comprise transferring cellular components including, but not limited to, nuclei, ribosomes, endoplasmic reticulum, Golgi apparatuses, lysosomes, peroxisomes, secretory vesicles, microfilaments, and microtubules.

The oocytes used in the methods and devices of the invention can be oocytes of any mammalian organism including, but not limited to, humans, mice, rats, apes, chimpanzees, orangutans, monkey, dog, cat, guinea pig, hamster, rabbits, ferrets, cows, horses, goats and sheep. In preferred embodiments, the oocytes are of human origin. In further preferred embodiments, the oocytes and the biomolecules and cellular components are from the same species. In yet further preferred embodiments, the biomolecules and cellular components are from the same individual.

Adult stem cells used in the methods of the invention include, but are not limited to, hematopoietic stem cells, mesenchymal stem cells, neural stem cells, epithelial stem cells, adipose stem cells, and skin stem cells. In some embodiments, menstrual blood derived cells are used as donor cells for biomolecules and cellular components and tunneling nanotube-forming cells in the methods of the invention.

The adult stem cells used in the methods and devices of the invention can be adult stem cells of any mammalian organism including, but not limited to, humans, mice, rats, apes, chimpanzees, orangutans, monkey, dog, cat, guinea pig, hamster, rabbits, ferrets, cows, horses, goats and sheep.

In preferred embodiments, the adult stem cells are of human origin. In further preferred embodiments, the adult stem cells and the oocytes are from the same species. In further preferred embodiments, the adult stem cells, the oocytes and the biomolecules and cellular components are from the same species. In yet further preferred embodiments the adult stem cells, the oocytes and the biomolecules and cellular components are from the same individual.

The menstrual blood derived cells used in the methods and devices of the invention can be menstrua; blood derived cells of any mammalian organism including, but not limited to, humans, mice, rats, apes, chimpanzees, orangutans, monkey, dog, cat, guinea pig, hamster, rabbits, ferrets, cows, horses, goats and sheep. In preferred embodiments, the menstrual blood derived cells are of human origin. In further preferred embodiments, the menstrual blood derived cells and the oocytes are from the same species. In further preferred embodiments, the menstrual blood derived cells, the oocytes and the biomolecules and cellular components are from the same species. In yet further preferred embodiments the menstrual blood derived cells, the oocytes and the biomolecules and cellular components are from the same individual.

In some embodiments, the oocytes used in the methods of the invention are obtained from the mammal after controlled ovarian stimulation. In some embodiments, controlled ovarian stimulation is not required because immature oocytes can be harvested and matured using the methods and devices of the instant invention. In such case, oocyte retrieval from the mammal can be done without the administration of gonadotropin, GnRH agonist or antagonist. In some embodiments, only hCG can be administered prior to oocyte retrieval.

In some embodiments, the oocytes used in the methods of the invention are immature oocytes retrieved from a mammal during an IVF procedure and designated to be discarded due to their immaturity.

In some embodiments, adult stem cells and/or menstrual blood derived cells are used as source for biomolecules and cellular components that are transferred to oocytes using the methods and devices of the invention.

In preferred embodiments, adult stem cells are used in autologous biomolecule and cellular component transfers and improve oocyte quality. The adult stem cells useful in the methods of the invention can be isolated from sources including, but not limited to, peripheral blood, bone marrow, adipose tissue, dental pulp, umbilical cord blood, menstrual blood and placenta. Adult stem cells can also be derived from peripheral blood mononuclear cells.

In preferred embodiments, peripheral blood is collected from a female autologous to the oocyte using tubes containing anti-coagulants including, but not limited to, heparin and EDTA-coated tubes. The peripheral blood is treated with red blood cell lysis buffer and the whole blood is separated into different fractions using density gradients including, but not limited to, ficoll-paque and histopaque gradients. The mononuclear cell layer is transferred to a petri dish after centrifugation, and the mononuclear cells are cultured in culture medium containing components including, but not limited to, 10-20% fetal bovine serum, autologous serum, human serum albumin, synthetic serum substitute and/or pooled human platelet lysate. The culture medium is renewed every 2-3 days until cell confluency is reached.

In an alternative embodiment, bone marrow is aspirated from the left iliac crest of a female autologous to the oocyte. Cells collected from bone marrow are cultured on a petri dish in culture medium containing components including, but not limited to, 10-20% fetal bovine serum, autologous serum, human serum albumin, synthetic serum substitute and/or pooled human platelet lysate. The culture medium is renewed every 2-3 days until confluency is reached.

In a further alternative embodiment, human subcutaneous adipose tissue is obtained from a female autologous to the oocyte by liposuction. Adipose tissue stem cells are isolated from the fat stromal vascular fraction by adherence to culture plates. The culture medium containing components including, but not limited to, 10-20% autologous serum, human serum albumin, synthetic serum substitute, fetal bovine serum and/or pooled human platelet lysate is renewed every 2-3 days until cell confluency is reached.

Advantageously, adult stem cells isolated using the methods of the invention can be cryopreserved in liquid nitrogen prior to autologous and/or allogenic biomolecule and cellular component transfer to oocytes. Cryopreserved stem cells are thawed and re-cultured in standard culture medium and conditions.

In preferred embodiments, tunneling nanotube-forming cells are injected as a spheroid. Spheroids are multicellular cell aggregates that form via extracellular matrices that link single cells together through integrin binding. Cell spheroids generally have a larger surface area when compared to single cell suspensions of the same type. A larger surface area promotes contact between tunneling nanotube-forming cells and oocyte. Also, tunneling nanotubes may be formed between cells in a spheroid and, therefore, increase the successful tunneling nanotube formation between tunneling nanotube-forming cells and oocyte, thereby improving oocyte quality.

In some embodiments, extracellular matrices, including, but not limited to, collagen IV are added to tunneling nanotube-forming cell culture prior to adding one or more oocyte to improve oocyte quality using the procedures of the invention. The culture method varies between different types of tunneling nanotube-forming cells according to specific cell type. In some embodiments, extracellular matrices that are useful in cell cultures of adult stem cells and/or menstrual blood derived cells are used. The skilled artisan can select an extracellular matrix suitable for the respective adult stem cell and/or menstrual blood derived cell. In some embodiments, cells are trypsinized and cultured in extracellular-matrix-containing medium prior to injection into the device of the instant invention. The duration of the culture varies and will result in different spheroid shapes and sizes. In some embodiments, tunneling nanotube-forming cells are cultured in culture medium comprising 1 mg/mL collagen IV for 20 minutes. In general, the concentration of extracellular matrices and time of culture may be inversely proportional. For example, the concentration of collagen IV can be from a low amount of about 1 μg/mL to a high amount of about 100 mg/mL. In some embodiments, the concentration of extracellular matrix can be about 2 μg/mL, about 5 μg/mL, about 10 μg/mL, about 20 μg/mL, about 50 μg/mL, about 100 μg/mL, about 200 μg/mL, about 500 μg/mL, about 1 mg/mL about 2 mg/mL, about 5 mg/mL, about 10 mg/mL, about 20 mg/mL, about 50 mg/mL to about 100 mg/mL.

The culture time for tunneling nanotube-forming cells in extracellular matrix can be from a low of 5 minutes to a high about 1 week. In some embodiments, the time of culture can be about 5 minutes, about 10 minutes, about 15 minutes, about 30 minutes, about 1 hour, about 2 hours, about 4 hours, about 5 hours, about 8 hours, about 10 hours, about 12 hours, about 18 hours, about 1 day, about 1.5 days, about 2 days, about 3 days, about 4 days, about 5 days, about 6 days, to about 1 week.

In some embodiments, the adult stem cells and/or menstrual blood derived cells of the invention are transfected with a vector carrying a KIF5B gene. KIF5B gene transfer to these cells results in the overexpression of KIF5B protein that is involved in distribution and transportation of biomolecules and cellular components. Advantageously, overexpression of KIF5B protein in adult stem cells and menstrual blood cells results in the formation of tunneling nanotubes in adult stem cells and menstrual blood derived cells. Also, overexpression of KIF5B protein in adult stem cells and menstrual blood cells increases the number of tunneling nanotubes formed by adult stem cells and menstrual blood derived cells.

In an alternative embodiment, by increasing the expression of a KIF5B protein in adult stem cells and menstrual blood derived cells the number of biomolecules and cellular components including, but not limited to, mitochondria transferred to an oocyte are increased. Advantageously, oocyte quality after enhanced biomolecule and cellular component transfer following KIF5B overexpression improves significantly. In some embodiments, a KIF5B protein is overexpressed by transfecting a plasmid containing an expression vector comprising the sequence of the KIF5B gene. The gene encoding the KIF5B protein can be from any mammalian and non-mammalian organism. In preferred embodiments, the KIF5B gene is a mammalian gene. In further preferred embodiments, the KIF5B gene is a human gene. The methods of cloning and transfection of genes and overexpression of proteins documented in the art can be used in the methods of the invention and these methods not described here in detail. In some embodiments, a KIF5B protein is supplemented to adult stem cells using microinjection or other protein injection techniques.

In some embodiments, methods and devices are provided for generating tunneling nanotube-forming cells. In specific embodiments, culture conditions and culture devices are provided that induce adult stem cells and/or menstrual blood derived cells to become tunneling nanotube-forming cells. In preferred embodiments, the tunneling nanotube-forming cells generated efficiently transfer biomolecules and cellular components to oocytes.

In specific embodiments, immature oocytes are cultured with cumulus cells surrounding each oocyte also known as cumulus-oocyte-complexes. In some embodiments, oocytes are denuded or isolated from other cell components by using hyaluronidase in phosphate buffered saline or culture medium. In some embodiments, mechanical stripping is used to facilitate denuding.

In some embodiments, oocytes are cultured with zona pellucida surrounding them. In other embodiments, the zona pellucida of oocytes is removed using methods including, but not limited to, mechanical stripping, Acidic Tyrode's solution, laser treatment, or treatment with pronase in culture medium. Advantageously, the removal of the zona pellucida can increase the number of biomolecules and cellular components transferred from tunneling nanotube-forming cells to oocytes through closer cell-cell contact.

Culture conditions used for oocytes and tunneling nanotube-forming cells include, but are not limited to, culture at 37° C. and 95% atmospheric air with 5% $CO_2$ in humid conditions, and include, but are not limited to, the addition of phosphate buffered saline around the culture and, optionally, mineral oil can be used to cover the culture.

Culture medium for oocytes and tunneling nanotube-forming cells is varied depending on the donor of the cells and cell conditions. A single media system or sequential media systems can be used for oocyte cultures to improve oocyte quality. The oocyte culture medium of the invention contains components including, but not limited to, salts, essential and non-essential amino acids and energy sources such as glucose. Culture media and culture conditions used generally for oocyte culture can also be employed in the methods of the instant invention.

In some embodiments, the culture medium of the invention contains one or more hormones. In preferred embodiments, the hormones used in the instant methods promote maturation and increase developmental competence of mammalian oocytes and include, but are not limited to, gonadotropic hormones, such as follicle-stimulating hormone (FSH), luteinizing hormone (LH), human menopausal gonadotropin (hMG), and human chorionic gonadotropin (hCG). In some embodiments, hMG and hCG can be substituted for FSH and LH respectively. In preferred embodiments, the concentrations of hormones are adjusted according to the cell quality, time in culture, proliferation status, and species of origin. The culture medium of the invention further contains serum supplements including, but not limited to, serum albumin, various growth factors that are essential for the growth of cultured cells. In some embodiments, fetal bovine serum (FBS) and serum from other individuals of the same species or serum from other species are used. In preferred embodiments, animal-free alternatives including, but not limited to, recombinant human serum albumin or a human patient's own serum are used in the methods of the instant invention. In a further preferred embodiment, 10% heat-inactivated serum of the human patient is supplemented in the culture medium used in the methods of the invention.

In some embodiments, the culture medium of the instant methods contains extracellular matrices. Extracellular matrix (ECM) is a non-cellular component that contains polysaccharides, growth factors and proteins. ECM functions as the structural support between cells and tissues, and is important in cell-cell interaction and biochemical support. In specific embodiments of the invention, addition of ECM to cell cultures creates an environment similar to in vivo environments and promotes cell growth. In some embodiments, extracellular matrix proteins including, but not limited to, collagen, elastin, fibronectin and laminin are added to the culture medium. In some embodiments, two or more types of extracellular matrix proteins are added to the culture medium. In preferred embodiments, low concentrations of extracellular matrix proteins are added into the culture medium while keeping the culture medium in liquid form instead of a gel to facilitate retrieval. In further preferred embodiments, about 1.5 mg/mL type I collagen is added in the culture medium of the instant invention. In further embodiments, collagen, elastin, fibronectin and/or laminin are added to the cell culture medium from a low of 0.1 mg/ml to a high of 20 mg/mL, or from about 0.2 mg/mL to about 18 mg/ml; from about 0.4 mg/mL to about 16 mg/mL; from about 0.6 mg/mL to about 14 mg/mL; from about 0.8 mg/mL to about 12 mg/mL; from about 1.0 mg/mL to about 10 mg/mL; from about 1.2 mg/mL to about 8 mg/mL; from about 1.4 mg/mL to about 6 mg/mL; from about 1.6 mg/mL to about 4 mg/mL; from about 1.8 mg/mL to about 4 mg/mL; or from about 2 mg/mL to about 3 mg/mL.

Referring to FIG. 1 shown is an instant invention that provides a hanging drop culture method to improve oocyte quality. For example, oocyte quality is improved in the hanging drop culture through the efficient transfer of biomolecules and cellular components to the oocyte using tunneling nanotube-forming cells. The three-dimensional hanging drop culture of the invention comprises a drop of culture medium comprising cells and/or tissues suspended from an inverted surface. In some embodiments, oocytes (6) and tunneling nanotube-forming cells (3) are cultured in a small droplet 2 such that the hanging drop minimizes the surface area to volume ratio of the culture medium and, thereby, reduces evaporation of culture medium and provides close proximity of oocyte and tunneling nanotube-forming cells for efficient tunneling nanotube formation. Advantageously, the hanging drop allows oocytes and tunneling nanotube-forming cells to gather in the middle of the drop due to gravity, maximizing the contact between the cells and maximizing the transfer of biomolecules and cellular components through the nanotubes of the tunneling nanotube-forming adult stem and menstrual blood derived cells.

In preferred embodiments, the drop of culture medium has a defined volume, comprises supplemented ECM proteins, serum and/or hormones, and is inverted on a plastic culture plate. For example, the volume of the drop can be from low of about 0.1 μl/drop to a high of about 200 μl/drop. The drop volume can further be from about 0.2 μl, 0.3 μl, 0.4 μl, 0.5 μl, 0.6 μl, 0.7 μl, 0.8 μl, 0.9 μl, and 1 μl to about 150 μl, 160 μl, 170 μl, 180 μl, and 190 μl and from about 1.2 μl to about 145 μl, about 1.5 μl to about 140 μl, about 1.7 μl to about 135 μl, about 2 μl to about 130 μl, about 2.5 μl to about 125 μl, about 3 μl to about 120 μl, about 3.5 μl to about 115 μl, about 4 μl to about 110 μl, about 4.5 μl to about 105 μl, about 5 μl to about 100 μl, about 6 μl to about 95 μl, about 9 μl to about 90 μl, about 10 μl to about 85 μl, about 11 μl to about 70 μl, about 12 μl to about 65 μl, about 13 μl to about 60 μl, about 14 μl to about 55 μl, about 15 μl to about 50 μl, about 16 μl to about 45 μl, about 17 μl to about 40 μl, about 18 μl to about 35 μl, about 19 μl to about 30 μl, about 20 μl to about 25 μl. In preferred embodiments the drop volume is about 10 μl to about 60 μl, about 15 μl to about 50 μl, or about 20 μl to about 45 μl. In further preferred embodiments, the drop volume is about 10 μl to about 40 μl. In most preferred embodiments, the drop volume is 20 μl.

In further preferred embodiments, the drop comprises one or more oocytes and about 1 to 50000 tunneling nanotube-forming cells (TNFCs). In more preferred embodiments, the drop comprises 1000 to 10000 tunneling nanotube-forming cells; in even more preferred embodiments, the drop comprises 4000 to 6000 tunneling nanotube-forming cells.

In some embodiments, the drop comprises one or more oocytes and from about 1 TNFC, 2 TNFCs, 4 TNFCs, 6 TNFCs, 8 TNFCs, 10 TNFCs, 15 TNFCs, 20 TNFCs, 25 TNFCs, 30 TNFCs, 40 TNFCs, 50 TNFCs to about 10000 TNFCs, 15000 TNFCs, 20000 TNFCs, 25000 TNFCs, 30000 TNFCs, 35000 TNFCs, 40000 TNFCs, and 50000 TNFCs. In some embodiments the drop comprises one or more oocytes and from about 500 to about 45000 TNFCs, from about 1000 to about 40000 TNFCs, from about 1500 to about 35000 TNFCs, from about 2000 to about 30000 TNFCs, from about 2500 to about 25000 TNFCs, from about 3000 to about 20000 TNFCs, from about 3500 to about 15000 TNFCs, from about 4000 to about 10000 TNFC, from about 4500 to about 8000 TNFCs, from about 5000 to about 6000 TNFCs, or any number of TNFCs encompassed by and between the recited ranges.

In some embodiments, the hanging drop is inverted on petri dish 1. In an alternative embodiment, the culture dish is coated with a material including, but not limited to, extracellular matrix, cell adhesion molecules, agar to promote oocyte and TNFC attachment. In preferred embodiments, the bottom of the petri dish 1 comprises a defined volume of culture liquid including, but not limited to, phosphate buffered saline, 0.9% NaCl, or other cell-compatible liquid to inhibit the evaporation of the culture medium droplet.

In some embodiments, the methods and devices of the invention provide small-scale culture systems. In some embodiments, the small-scale culture systems comprise a miniature-volume culture system that, in some embodiments, comprises less than 20 μL of internal total volume and medium. For example, the volume of the small-scale cell culture system can be from low of about 0.1 μl to a high of about 100 μl. The volume can further be from about 0.2 μl, 0.4 μl, 0.6 μl, 0.8 μl, 1 μl, 1.2 μl, 1.5 μl, 2 μl, and 2.5 μl to about 95 μl, 90 μl, 85 μl, 80 μl, and 75 μl and from about 0.2 μl to about 50 μl, about 0.4 μl to about 45 μl, about 0.6 μl to about 40 μl, about 0.8 μl to about 35 μl, about 1 μl to about 30 μl, about 1.2 μl to about 25 μl, about 1.4 μl to about 20 μl, about 1.4 μl to about 18 μl, about 1.6 μl to about 16 μl, about 1.8 μl to about 14 μl, about 2 μl to about 12 μl, about 2.2 μl to about 10 μl, about 2.4 μl to about 8 μl, about 2.5 μl to about 6 μl, and about 0.1 μl to about 5 μl, about 0.2 μl to about 4.5 μl, about 0.4 μl to about 4.5 μl, about 0.6 μl to about 4 μl, about 0.8 μl to about 3.5 μl, about 1 μl to about 3 μl, about 0.5 μl to about 1.5 μl, about 0.75 μl to about 1.25 μl, or about 1 μl.

In preferred embodiments the small-scale culture volume is about 0.1 μl to about 5 μl. In further preferred embodiments, the small-scale culture volume is about 1 μl.

Advantageously, the small-scale culture systems of the invention allow a close contact between an oocyte and one or more tunneling nanotube-forming cells and minimize waste of culture medium. The small-scale culture systems of the instant invention include, but are not limited to, open systems including, but not limited to, hanging drop and droplet-based cell culture systems and closed systems including, but not limited to, microfluidics.

In some embodiments, microfluidic devices are provided to improve oocyte quality through autologous biomolecules and cellular components transfer from tunneling nanotube-forming cells. Microfluidic device generally refers to sub-millimeter scale device that provides precise fluid manipulation. It may be used in biology and medical applications and provide controlled environment for cell culture and growth. Advantageously, cells inside the microfluidic device of the invention are less affected by the external environment and would have a lower batch to batch variation. Since microfluidic devices are usually of microliter-scale, they minimize the amount of tunneling nanotube-forming cells and medium used in the invention.

In specific embodiments, the microfluidics systems of the invention are manufactured of materials that include, but are not limited to, polydimethylsiloxane (PDMS) and polymethyl methacrylate (PMMA). Any materials suitable to manufacture microfluidic devices are envisioned to be used to manufacture the microfluidic devices of the instant invention.

In preferred embodiments, a clear and transparent material is used to allow real-time monitoring on the stage and condition of oocytes in the embodiment. The microfluidic devices of the instant invention can be manufactured using standard lithography techniques followed by casting and curing of the polymers. In preferred embodiments, the microfluidic device is fabricated using soft-lithography techniques, followed by casting and curing of PDMS prepolymer. SU-8 3025 can be used as the PDMS polymer by mixing preferably 10:1 base to curing agent, followed by curing at 60-70° C. to manufacture a microfluidic chip. The microfluidic chip of the invention can be adhered to a cover slip using PDMS polymer of 2:1 base to curing agent, and heated on a heat plate at preferably 170° C. The curing temperature and ratio of base to curing agent can be changed according to the need of user.

In preferred embodiments, the microfluidic devices of the invention comprise at least two openings connected to a closed space. In further preferred embodiments, the volume of the closed space in the microfluidic device is such that it preferably holds enough culture medium for oocyte maturation while being small enough to promote close cell-to-cell contact between an oocyte and one or more tunneling nanotube-forming cells. Advantageously, the microfluidic devices of the invention allow precise fluid manipulation and a precise control of the environment for optimal cell culture and growth. Furthermore, the cells inside the microfluidic device are less affected by the external environment than under conventional culture conditions and the cultured cells have a lower batch-to-batch variation. In some embodiments, a microfluidic device of the invention has a closed space with a diameter of about 100 µm to about 2 mm diameter and a height of about 10 µm to 200 µm. In some embodiments, the closed space of the microfluidic device of the invention has a diameter from about 120 µm, about 140 µm, about 160 µm, about 180 µm, about 200 µm to about 1.6 mm, 1.8 mm, 2 mm and a height from about 15 µm, about 20 µm, about 25 µm, about 30 µm, about 35 µm, about 40 µm to about 100 µm, about 120 µm, about 140 µm, 160 µm, about 180 µm, or about 200 µm. In preferred embodiments, the closed space of the microfluidic device has a diameter of about 100 µm to about 1.5 mm or about 150 µm to about 1.2 mm and a height of about 20 µm to about 180 µm or 30 µm to about 160 µm. In further preferred embodiments, the closed space of the microfluidic device has a diameter of about 200 µm to about 1 mm and a height of about 40 µm to about 150 µm.

In preferred embodiments, the dimensions of the microfluidic device of the invention are chosen to adjust to the condition and volume of the tunneling nanotube-forming cells and oocytes used. The shape of the closed space varies. In some embodiments, the closed space is a cube, a cuboid, a cylinder, a cone, a tetrahedron, a triangular prism, a square pyramid, an octahedron, a dodecahedron, an icosahedron, an hexagonal prism, a hexagonal pyramid, a pentagonal prism, a pentagonal pyramid, an octagonal prism, or an ellipsoid. In preferred embodiments, the closed space of the microfluidic device of the invention is a cylinder.

In some embodiments, the surface of the culture system may be coated with collagen. Collagen may be coated on a plate, membrane or any surface that is suitable for cell culture. The concentration or amount of collagen may vary depending on cell status, culture system surface or other factors. Collagen coating may provide better attachment and growth for cells, which may result in an improvement of oocyte quality and maturation.

Figure 2A:
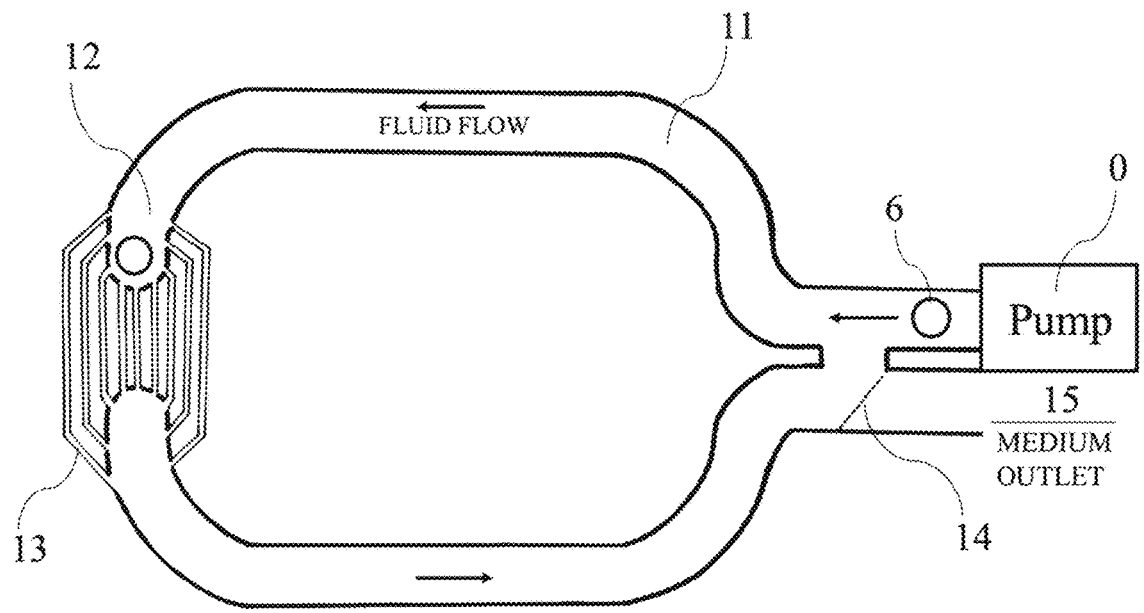
FIG. 2(a) shows a top view of the microfluidic device of the invention with preferred channels and microchannels for maximizing tunneling nanotube formation.

Referring to FIG. 2(a) shown is the top view of a preferred embodiment of a microfluidic tunneling nanotube formation device of the invention used in the transfer of autologous biomolecules and cellular components between one or more oocytes and tunneling nanotube-forming cells. The microfluidic tunneling nanotube formation device includes one or more channels (11), a microchannel system (13) comprising a plurality of microchannels, and at least one reaction chamber (12). In a channel (11), at least one oocyte may be placed and flowed towards a reaction chamber (2), where the at least one oocyte remains or sets.

Desirably, living cells, including but not limited to oocytes and tunneling nanotube-forming cells do not adhere to channel (11), reaction chamber (12) and/or microchannel system (13) of the microfluidic device that is made of a material including, but not limited to, polydimethylsiloxane. Instead, the living cells set or flow freely in a fluid or medium within the channel and microchannel systems. Such microenvironment better mimics an in vivo environment. For example, an embryo migrates in vivo from the oviduct to the uterus without adhesion to the side of the oviduct. In some embodiments of the instant invention, larger cells such as oocytes sink to the bottom of a channel and/or chamber of the device without adhesion to said channel and/or chamber. The movement of larger cells within the device may, therefore, require control of the fluid dynamics such that the fluid flow moves the larger cells within the channels and/or chamber. Although the microfluidic device of the invention can be made of any material generally used to manufacture cell culture devices, preferred materials for the manufacture of the microfluidic devices of the invention are materials that do not allow cell attachment to their surfaces. However, if tunneling nanotube forming cells adhere to the material of the microfluidic device, the cells can be removed from said surface using trypsin or other cell dissociation methods known in the art.

In the embodiment of FIG. 2(a), at least one inlet is located at the front end of channel (11). In preferred embodiments, the size of the inlet is generally larger than the diameter of the fluid manipulating device, such as, e.g., a tip of a micropipette or adjustment handle. The size of the inlet depends on the material and tube used to inject and manipulate the cells and medium, and is configured so as to fit tightly with the fluid manipulating device to allow fluid and cells to enter channel (11) and to avoid that fluid and cells flow out of the inlet due to lower resistance. The inlet of the channel can be in the same direction of the channel or can be tilted towards the top for easier handling. In preferred embodiments, a vertical inlet with a 90 degree turn into the channel is used for easier production using a punch, therefore, the shape of the inlet is usually cylindric. In other embodiments, such as when the inlet is produced from the side, a "V" shape with a wider end away from channel (11) is used to facilitate the handling and adding of medium with or without cells into the system.

In some embodiments, channel (11) is connected from an inlet, optionally through the pump 0 to reaction chamber (12) and microchannel system (13). The height and width of the channel varies depending on the size of the cell used in the system. The dimensions of the channel can be changed depending on the requirements of the user, for example, a narrow channel of one cell wide can allow cells to pass through in a single file, such that tunneling nanotubes can be visualized easily. In preferred embodiments, channel (11) is straight with smooth round corners to allow laminar flow. In further embodiments, channel (11) has different shapes as long as laminar flow is maintained. Longer and curved channels may be used to allow smooth entry of cells and oocytes, and provide a medium reservoir. Constrictions and valves can also be added into channel (11) to control the flow of the device. In preferred embodiments, an active flow is maintained for medium renewal. In some embodiments, the flow may be stopped to allow cells to interact and form tunneling nanotubes.

In some embodiments, reaction chamber (12) allows cells, including but not limited to tunneling nanotube-forming cells and oocytes, to interact and form tunneling nanotubes. In some embodiments, one or more reaction chamber can be designed to allow tunneling nanotubes to form between cells simultaneously.

In preferred embodiments, the reaction chamber is circular to maximize the usage area for tunneling nanotube formation, since a lot of cells appear in circular shape when they are in suspension. In further preferred embodiments, the size of the reaction chamber is not narrower than channel (11), such that there is no or minimal resistance to inhibit cells to enter and pass through. In more preferred embodiments, the reaction chamber is designed as a continuation of channel (11) without any separation.

In some embodiments, the reaction chamber is large with more than twice the diameter of channel (11) to inhibit an escape of the oocyte. In further embodiments, a valve is added between channel (11) and reaction chamber (12) to trap the oocyte and tunneling nanotube-forming cells within the reaction chamber, such that the small area maximizes tunneling nanotubes formation. The valve can also serve as the boundary of channel (11) and reaction chamber (12).

In some embodiments, the microchannel system (13) is located downstream of the reaction chamber (12) and upstream of the outlet. Advantageously, when tunneling nanotube-forming cells and oocytes are inserted to the microfluidic device, the microchannel system can separate the cells based on their properties, such as size. In a preferred embodiment, when the sample includes at least one oocyte and tunneling nanotube-forming cells, because MSCs/tunneling nanotube-forming cell are about 10-40 μm in diameter and oocytes are about 80-100 μm in diameter, the microchannels can be adjusted to a diameter between a tunneling nanotube-forming cell and an oocyte such that the tunneling nanotube-forming cells can pass through the microchannel and be retrieved from the outlet while the at least one oocyte is trapped in the reaction chamber.

In some embodiments, the microfluidic device of the invention comprises a single microchannel (13). In other embodiments, the microfluidic device of the invention comprises a microchannel system (13) comprising multiple microchannels for efficient filtering. Advantageously, the multiple microchannel system allows filtering even in the presence of formation of cell clusters that would be trapped in narrow microchannels and completely block a single microchannel system. More microchannels are preferred in the embodiment, such that even when cells have jammed one microchannel, other microchannels can still be used for cell removal. An important factor is the width of all microchannels (13) combined. The sum of width of microchannels (13) should not be smaller than the width of channel (11) because if the sum of width of the microchannel (13) was much less than that of channel (11), a high pressure in the upstream portion of the microfluidic would result. In that case, the cells in the said embodiment would be exposed to, among others, mechanical stress conditions and would exert cellular stress responses. In the worst case, the cells may burst.

Further, if the sum of width of all microchannels (13) is much smaller than the width of channel (11), larger cells may squeeze through microchannel (13) and be removed from outlet instead of being trapped in reaction chamber (12) due to the increased pressure and faster flow rate at reaction chamber (12) and individual microchannels (13).

In preferred embodiments, the flow rate in the microfluidic system of the invention is slow such as, e.g., <10 μL/minute, more desirably <5 μL/minute to inhibit the larger cells to be flushed out from reaction chamber (12) through the microchannels (13).

If the cells used in embodiment have similar sizes, cell properties other than cell size can be used to separate the cells. For example, in some embodiments, microbeads and antibodies to different surface proteins are used to separate different types of cells. In some embodiments, magnetic beads are added into the channel through the outlet. As the fluid containing the magnetic beads is continuously pumped into the embodiment, the magnetic beads can be captured by a magnet placed outside the microchannel system (13) to hold the magnetic beads in place. In this embodiment, the magnetic side of the bead faces towards the magnet present on the outside of the channel while the antigen binding region faces towards the inner side of the microchannel. In preferred embodiments, when cells are injected, a target type of cells is captured by cell-specific beads allowing the other types of cells to pass through. Eventually, the captured cells can be collected by removing the magnet and flushing the microchannel(s) with fluid.

In some embodiments, active flow may be used in the microfluidic device for renewal of nutrients and cells. Pump 0 is used to generate the active flow in the microfluidic device. In some embodiments as shown in FIG. 2(a), a syringe pump is connected externally of the microfluidic device, and the outlet of the pump is linked to the inlet of the microfluidic device. In other embodiments, smaller pumps that fit into a microfluidic device are used for easier handling. In a embodiments as shown in FIG. 2(a), a slow flow rate is desired because tunneling nanotube formation and transfer is a process that takes minutes to hours, so that a low flow rate ensures that at least one oocyte is pushed away from tunneling nanotube-forming cells before the formation of tunneling nanotube. In other embodiments, the flow rate is varied to different flow rates during the addition of medium and cells. Advantageously, the benefit of an active flow is that the amount of medium and nutrients can be relatively limited because of the micron-width of the channels and microchannels in the microfluidic device. However, the concentration of waste and toxic substances released by cells in the microfluidic device may increase faster than in other systems with larger volume due to limited volume of medium and space. In preferred embodiments, the medium is therefore continuously renewed in the microfluidic device of the invention to improve cell viability. In further embodiments, the medium is submitted to active flow such that the flow allows movement of cells in the microfluidic device. Advantageously, the linear and rotational movement of the oocytes in the microfluidic system resulting from such medium flow improves oocyte quality.

In some embodiment, such as the embodiment shown in FIG. 2(a), an optional filter (14) is used to retain cells in the microfluidic device circulation while used medium is removed from the microfluidic device. In some embodiments, the filter is located upstream of outlet 15 in the microfluidic device, such that the cells trapped inside the microfluidic device can circulate back to channel (11). In alternative embodiments, a filter is installed externally of the microfluidic device for larger surface area and higher filter efficiency. In preferred embodiments, the pores of the filter are smaller than the diameter of any cell used in the microfluidic device. For example, when tunneling nanotube-forming cells of 20-50 μm cell diameter are used in the system, a filter with pores smaller than 15 μm is used. In some embodiments, the channels can be blocked by setting polydimethylsiloxane barriers of sizes smaller than 15 μm within the channels. In further embodiments, alternative methods based on cell properties other than size are used to separate and retain the cells. For example, in some embodiments cell shape, cell density or magnetic properties of cells are used to separate and retain the cells.

Figure 2B:
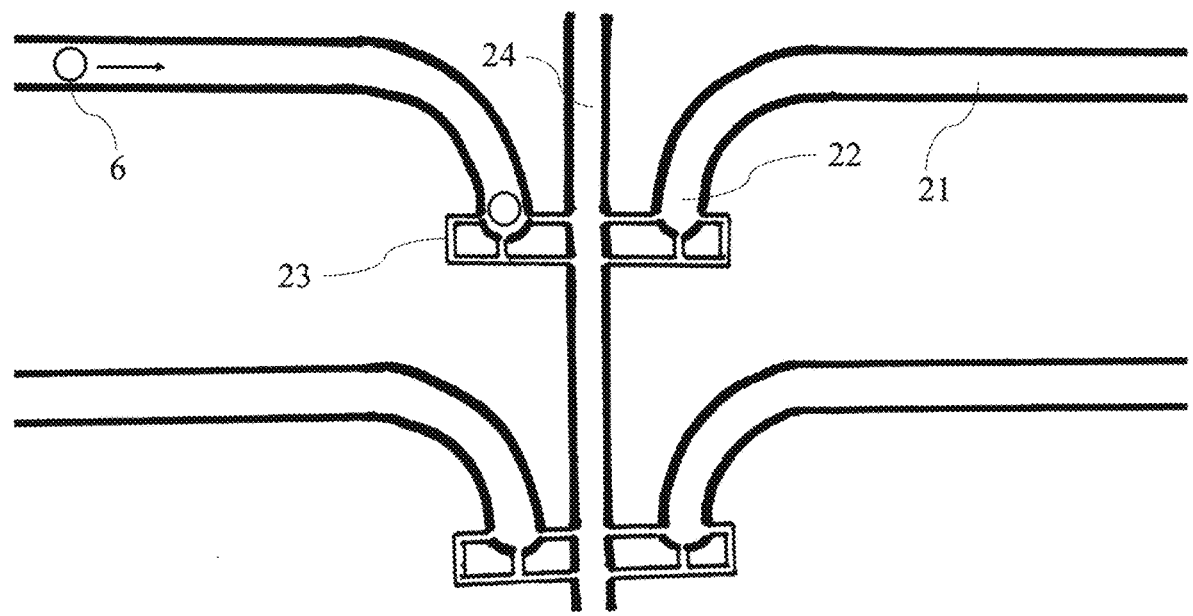
FIG. 2(b) shows a top view of an alternative microfluidic channel with channels and microchannels for maximizing tunneling nanotube formation for multiple tunneling nanotube formation reactions.

Referring to FIG. 2(b) shown is the top view of a further embodiment of a microfluidic tunneling nanotube formation device of the invention. In preferred embodiments, channel (21) is connected from the inlet to reaction chamber (22). The width of channel 21 is at least the diameter of an oocyte 6 plus two times the diameter of a tunneling nanotube-forming cell. Thus, in preferred embodiments, the width of channel (21) is at least 100 µm. In some embodiments, the width of channel 11 is from a low of 50 µm to a high of 500 µm; from about 55 µm to about 450 µm; from about 60 µm to about 400 from about 65 µm to about 350 from about 70 µm to about 300 from about 75 µm to about 250 from about 80 µm to about 200 from about 85 µm to about 150 from about 90 µm to about 125 µm. Advantageously, due to the width of the channel (21), the resistance to cell and medium injections is low such that no damage of cells due to any force exerted during injection of cells and medium will occur.

In preferred embodiments, channel (21) comprises a turn such that the large oocyte 6 is trapped in reaction chamber (22), which inhibits oocyte 6 from refluxing back to the outlet. In preferred embodiments, a right angle turn with smooth edges is provided to maintain the flow while inhibiting cell trapping at the turn.

In some embodiments, reaction chamber (22) is connected to at least one microchannel (23). In preferred embodiments, the at least one microchannel (23) is narrower than channel (21), with a diameter between the size of a larger cell, e.g., oocyte and smaller cell, e.g., tunneling nanotube-forming cell used in the system such that an oocyte (6) can be trapped in the reaction chamber (22), while the smaller tunneling nanotube-forming cells pass through. Advantageously, the microfluidic device of the invention allows the sorting of two types of cells by size. In other embodiments, other cell properties and methods are used to sort and separate the cells, including, but not limited to, the presence of specific membrane proteins on the cell surface that are bound buy specific antibodies and magnetic beads.

In some embodiments, multiple microchannels (23) are connected to a reaction chamber (22) from different angles and directions. In preferred embodiments, at least three microchannels are connected to a reaction chamber (22).

In further embodiments, the microchannels (23) are connected to a central channel (24) that is connected to an outlet for cell and medium removal. In some embodiments, the microchannels are connected to the central channel (24) from different directions such that the microfluidic device of the invention comprises turns and merges microchannels (23) for their connection to a central channel (24). In preferred embodiments, the turns are smooth turns to inhibit cells from clustering at the turn. In further preferred embodiments, the central channel (24) is a wide channel that is connected from at least one microchannel (23) to at least one outlet.

Figure 3:
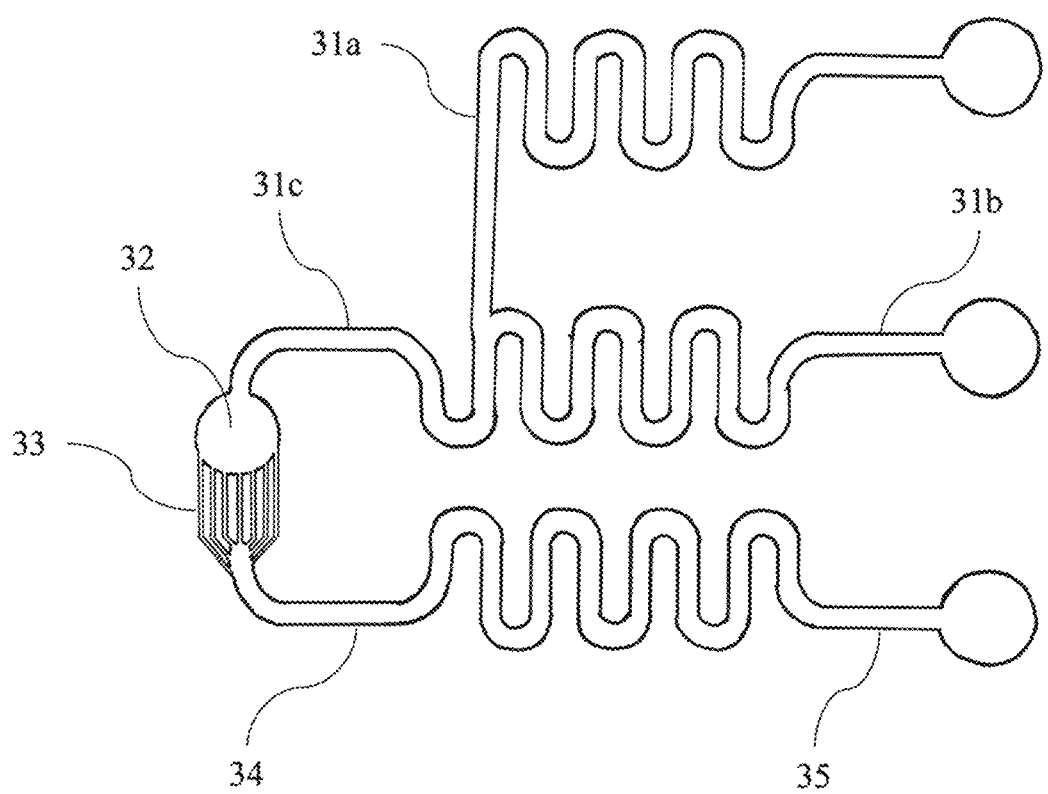
FIG. 3 shows a top view of another alternative microfluidic device of the invention with preferred channels and microchannels for maximizing tunneling nanotube formation.

Referring to FIG. 3 shown is an alternative embodiment of a microfluidic tunneling nanotube formation device used in a microfluidic cell co-culture system.

In the depicted embodiment, multiple inlets and channels (31a-b) are designed to connect a reaction chamber (12) from two sides. In preferred embodiments, the inlet and channels are evenly spread or identical. In other embodiments, other arrangements allow easier operation with different distances between channels (31a), (31b) and outlet (35). In the preferred embodiment, oocyte and tunneling nanotube-forming cells are injected separately from inlets upstream of two channels (31a) and (31b). The two inlets are interchangeable, meaning there is no particular choice which cell type has to be injected through which inlet. Channels (31a) and (31b) may be merged into one channel (31c) before connected to reaction chamber (32), or may be directly connected to a reaction chamber (32) without merging together into one channel. The width of the merged channel (31c) is preferred to be wider than or equivalent to the width of either channel (31a) or (31b). The curved channels (31a) and (31b) allow smooth injection of the cells and oocytes.

In the embodiment, an automated pump is used to inject tunneling nanotube-forming cells and oocyte into a microfluidic tunneling nanotube formation device. In the preferred embodiment, oocyte and tunneling nanotube-forming cells are injected into the device simultaneously. Advantageously, a multichannel syringe pump assists by pumping the said cell types at the same time. After transferring the oocyte and tunneling nanotube-forming cells into two different syringes, the said syringes are placed onto the multichannel syringe pump, and the cells are injected into the microfluidic tunneling nanotube formation device. The oocyte and tunneling nanotube-forming cells will enter the reaction chamber 32 via channels 31a, 31b and 31c. In an alternative embodiment, the oocyte and tunneling nanotube-forming cells are injected separately. A manual injection device or automated pump may be used when cells are injected separately. It is preferred that the oocyte is injected prior to the injection of the tunneling nanotube-forming cells, so the oocyte will be trapped at the reaction chamber 32 during the injection of the tunneling nanotube-forming cells, which may pass through microchannel 33. The reverse order may also function similarly when handled with caution.

Figure 4:
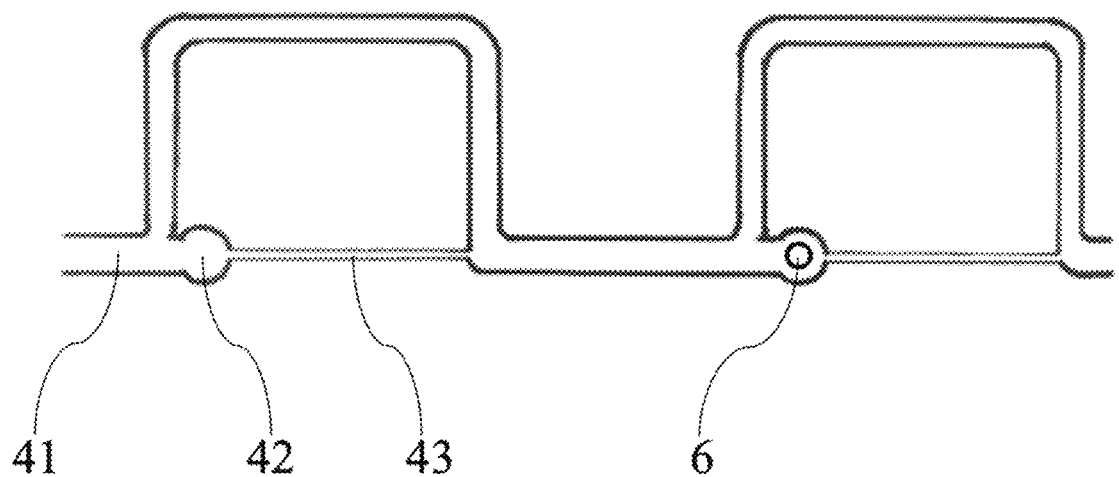
FIG. 4 shows an alternative microfluidic channel layout of a device of the invention showing a design for oocyte trapping and cell-cell interaction.

Referring to FIG. 4, in some embodiments a further design of a microfluidic tunneling nanotube formation device of the invention is provided that is used in a microfluidic cell co-culture system. In some embodiments, one or more cell is trapped in at least one reaction chamber (42), while other cells are passed through at least one channel (41). In some embodiments, microchannel (43) connects the reaction chamber (42) to the downstream channel.

In some embodiments, at least one reaction chamber (42) is located directly at the turn of a channel, where one or more oocytes (6) from the same patient can be loaded into the reaction chamber by controlling the flow rate. In some embodiments, another batch of cells comprising tunneling nanotube-forming cells is then injected into the channel of the device. Advantageously, the cells located near the reaction chamber (42) interact with the first batch of tunneling nanotube-forming cells and form tunneling nanotubes. In some embodiments, to remove an oocyte (6) trapped in the reaction chamber (42), medium or fluid is injected from the outlet, such that the fluid flows into the reaction chamber (42) through the microchannel (43) and oocyte (6) is pushed out and collected at the inlet. Advantageously, this design allows a large number of reaction chambers (14) to be connected together for tunneling nanotube formation studies, theoretically hundreds to thousands simultaneously.

The invention is further illustrated by reference to the following non-limiting examples.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Effect of Tunneling Nanotube-Forming Cells on Mouse Oocytes Using a Hanging Drop Culture System The effects of autologous biomolecules and cellular components transfer to mouse oocytes using hanging drop method in in vitro maturation were assayed. 6-week-old or 12-month-old C57/BL6 mice were primed with PMSG (5 IU/female). The female mice were sacrificed 48 hours later by cervical dislocation. Alcohol was sprayed to the abdominal region of the mice, and an incision was made to expose the abdominal cavity. The ovaries were dissected and diced using a needle. Germinal vesicle (GV) oocytes were selected and were subjected to either control (medium only) or co-culture with adult stem cells. Prior to co-culture, cumulus cells around oocytes were removed using 1 mg/µl hyaluronidase in M2 medium (Sigma-Aldrich, USA).

To mimic poor oocyte quality such as such as by inhibiting mitochondrial respiratory function, oocytes were treated with 0.05 µM concentration of rotenone for 2 hours. The oocytes were collected after 24 hours of co-culture.

Adult stem cells were collected from the adipose tissue prior to in vitro maturation. C57/BL6 mice were sacrificed by cervical dislocation. Five mg of subcutaneous fat were dissected from the mice. After cutting into small pieces, subcutaneous fat was subjected to type I collagenase (2 mg/mL in PBS, Thermo Fisher Scientific, USA) digestion in 37° C. for one hour. The sample was then centrifuged at 400 g for 15 minutes, and the stromal vascular fraction was collected and cultured on a petri dish in DMEM low glucose medium (Thermo Fisher Scientific, USA) supplemented with 20% fetal bovine serum (Thermo Fisher Scientific, USA) and 1% Penicillin/Streptomycin (Thermo Fisher Scientific, USA) until cell confluency was reached. The culture medium was changed every 2-3 days. Prior to co-culture, mitochondria of adult stem cells were labelled with mitotracker green. In another preparation of adult stem cells, adult stem cells are transfected with plasmid containing a mcherry-labelled LC3 autophagosome gene. Expression of LC3-mCherry in adult stem cells is confirmed by flow cytometry.

IVM culture medium was prepared using Alpha MEM without amino acids (except glutamine), vitamins and nucleosides. The simplified Alpha MEM containing 10% FBS and 0.2 IU/mL FSH was freshly prepared. Selected oocytes were washed three times in M2 medium and were cultured in a hanging drop composed of 20 µl IVM culture medium with and without 5000 suspended adult stem cells for the treatment group and control group respectively at 37° C. under 5% CO2 in humidified air. After 24 h co-culture, 0.25% trypsin (Life Technologies, USA) was used to detach MSCs on oocytes. Oocytes with polar bodies were recorded as mature oocytes.

Results

Figure 5A:
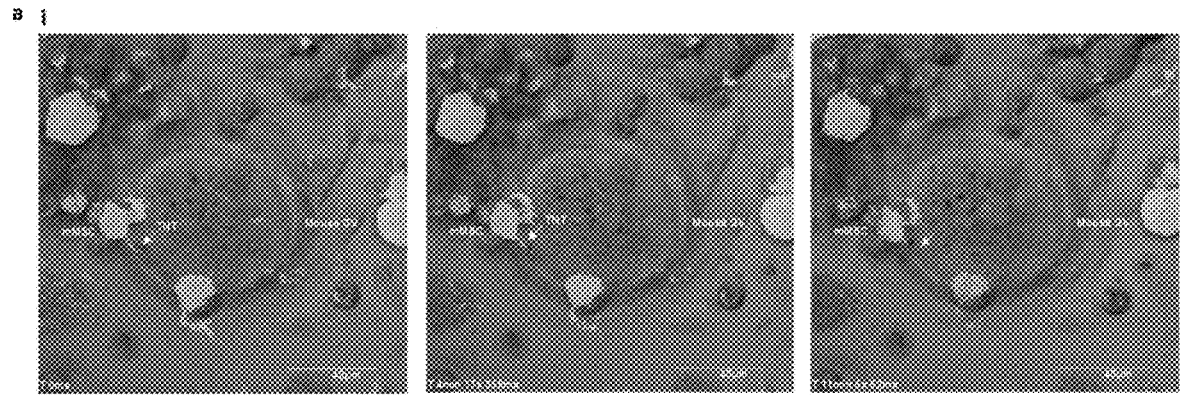
FIG. 5(a) shows a series of z-stacked laser confocal microscopy images showing a biomolecule and cellular component transfer from a mouse adult stem cell (mMSC) to a mouse germinal vesicle (GV) oocyte through a tunneling nanotube (TNT). Mitochondria in adult stem cells are labelled with mitotracker. The arrow shows mitochondria being transferred into the mouse oocyte through a tunneling nanotube.
Figure 5B:
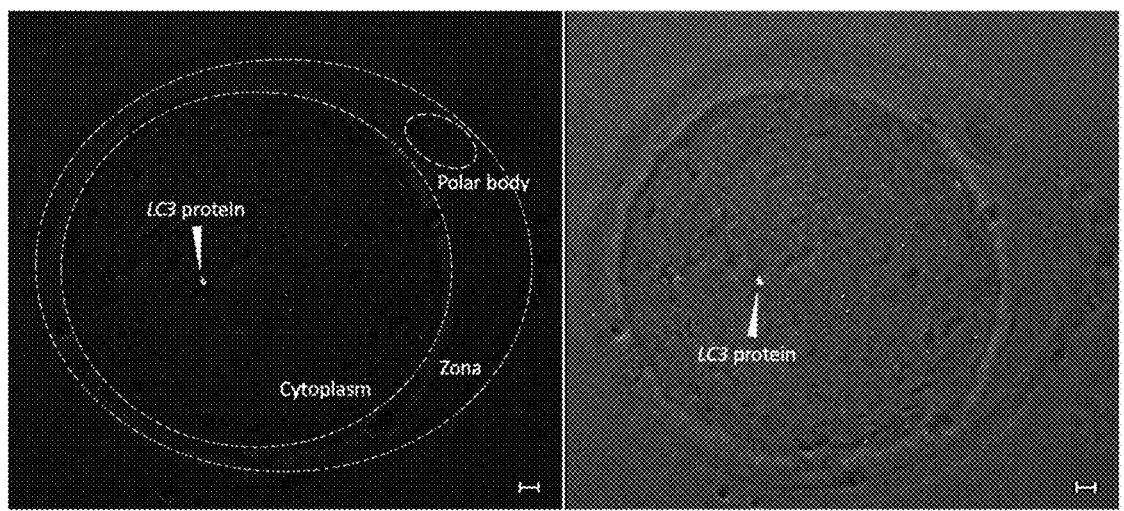
FIG. 5(b) shows two confocal microscopy images of a mouse oocyte after a biomolecule and cellular component transfer from a mouse adult stem cell (mMSC). LC3 autophagosome proteins are labelled with mCherry fluorescent protein. The arrows show LC3 that has been transferred into the mouse oocyte through a tunneling nanotube.
Figure 6:
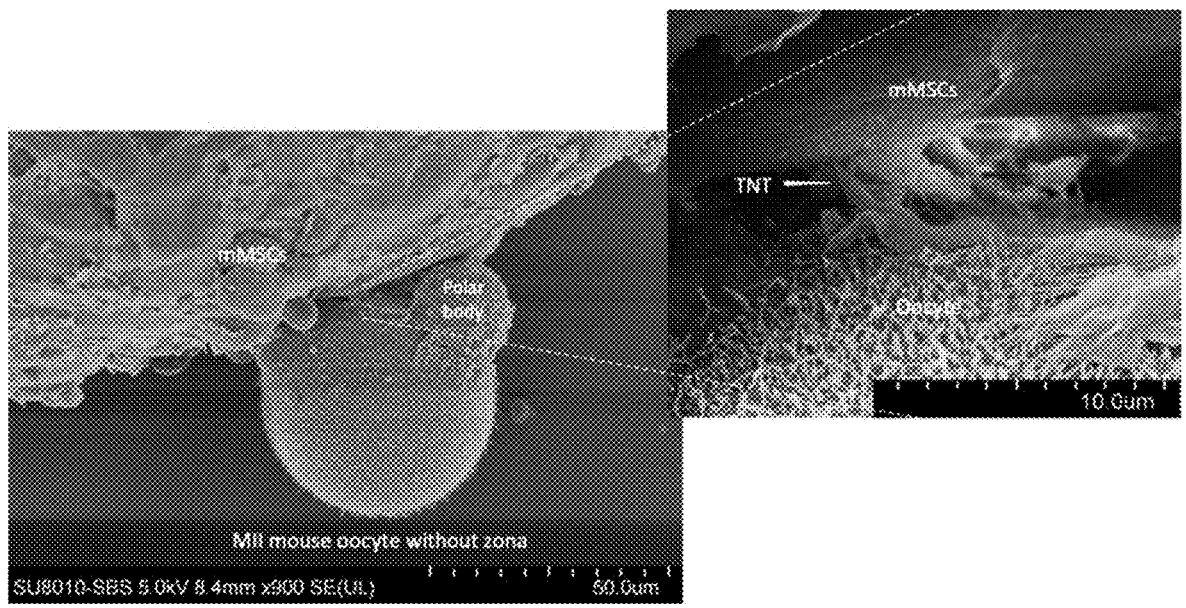
FIG. 6 shows two scanning electron microscopy images of a mouse adult stem cell (mMSC), a meiosis II mouse oocyte and the structure of a tunneling nanotube (TNT) in high magnification.

To confirm the successful transfer of mitochondria from adult stem cells to at least one oocyte, mitochondria of adult stem cells were labelled with mitotracker green before co-culture. The presence of a mitotracker green signal in oocytes confirmed that adult stem cells have donated mitochondria from adult stem cells to oocytes through tunneling nanotubes (FIG. 5(a)). To confirm the transfer of proteins from adult stem cells to at least one oocyte, a plasmid containing fluorescent protein-tagged autophagosome was transfected to adult stem cells before co-culture. The presence of mCherry red signal in oocytes confirmed that adult stem cells have transferred protein from adult stem cells to oocytes through tunneling nanotubes (FIG. 5(b)). Tunneling nanotubes between adult stem cells and oocytes were formed within 2 hours of culture. Tunneling nanotubes penetrated the oocyte zona pellucida and were in close contact with the cytoplasm of the oocyte. Scanning electron microscopy also confirmed that tunneling nanotubes were connected from adult stem cells to oocytes (FIG. 6).

Figure 7:
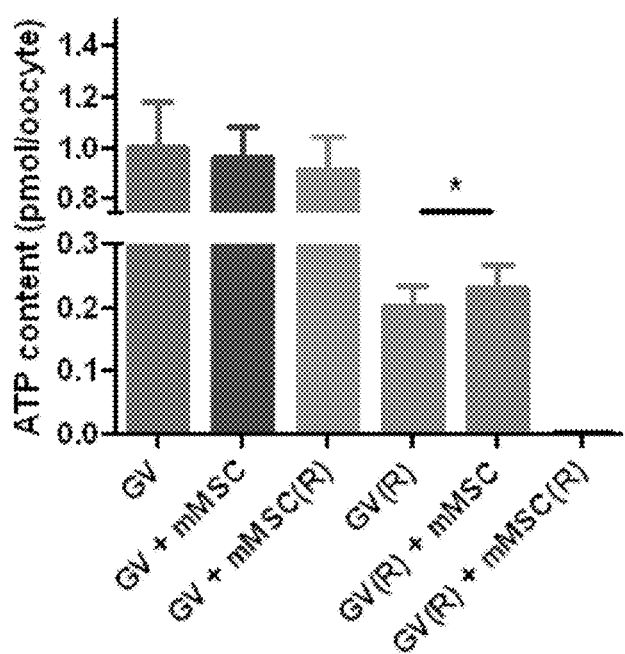
FIG. 7 shows a graph of the ATP levels of oocytes without (GV) and with biomolecule and cellular component transfer (GV+mMSC) and cells treated with rotenone (R).

To demonstrate the effect of mitochondria, biomolecules and cellular components transfer on improving oocyte quality with mitochondrial dysfunction, intra-ATP content of mitochondrial-transferred and non-mitochondrial-transferred oocytes following germinal vesicle breakdown (GVBD) were studied. The results showed that mouse MSCs (mMSC) increased ATP content of Rotenone-treated oocytes (GV(R)) by 13.3% (FIG. 7). Moreover, when mMSCs were treated with Rotenone, the ATP content of GV with mitochondrial dysfunction was markedly lowered to below 0.1 pmol/oocyte.

Figure 8:
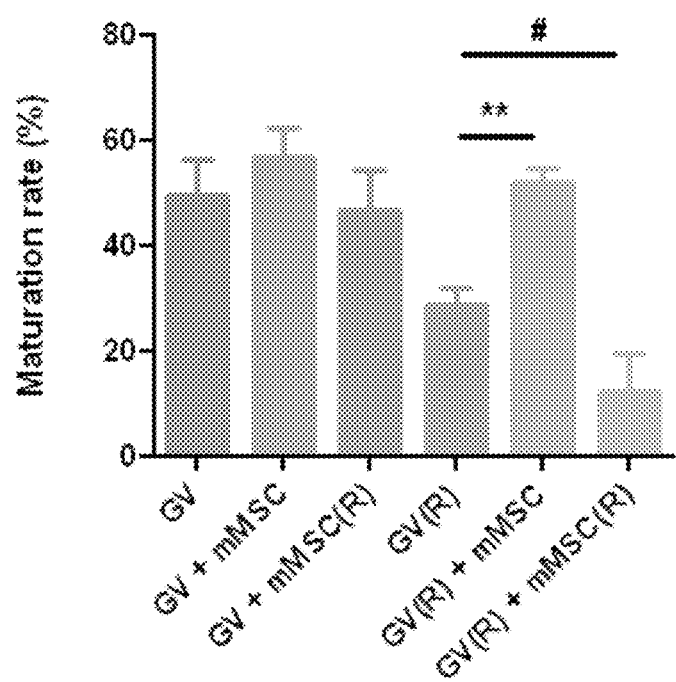
FIG. 8 shows a graph summarizing the maturation rate of oocytes without (GV) and with biomolecule and cellular component transfer (GV+mMSC) and cells treated with rotenone (R).

To study how mitochondrial transfer from adult stem cells to oocytes supports oocytes maturation with mitochondrial dysfunction, the maturation rates of oocytes with or without mitochondrial transfer were compared. Maturation rates of oocytes after being treated with rotenone was reduced dramatically but significantly increased by 80.4% after mMSCs mitochondrial transfer (FIG. 8). These results indicated that mMSCs could support germinal vesicle breakdown and maturation of GV(R) through mitochondrial transfer and ATP content enhancement. Nevertheless, MSC with mitochondrial dysfunction did not support GV(R) maturation and significantly reduced the rate by 56.7%.

To study how mitochondrial transfer improves oocyte quality from aged mice, oocytes from 12-month mice were used. Mitochondrial transfer from aged adult stem cells led to an increase in maturation and fertilization rate by 59.3% and 50.0% respectively (Table 1). The number of ≥6-cell embryos also increased by 50% after mitochondrial transfer. At the same time, polar body fragmentation rate, which is a marker for poor oocyte quality, was lowered by 58.6% after autologous mitochondrial transfer.

TABLE 1

|  | Control group (12m-GV) | MSC group (12m-GV + 12m-mMSC) | Improvement |
|---|---|---|---|
| Maturation rate (%) | 29/77 (37.7) | 39/65 (60) | +59.3** |
| Fertilization rate (%) | 4/15 (26.7) | 8/20 (40) | +50.0 |
| Cleavage rate at day 1-2 (%) | 3/4 (75) | 6/8 (75) | 0.0 |
| ≥6-cell at day 3-4 (%) | 1/4 (25) | 3/8 (37.5) | +50.0 |
| Abnormal PB (%) | 5/30 (16.7) | 2/29 (6.9) | −58.6 |

Example 2

Effect of Overexpressing KIF5B in Adult Stem Cells on Mouse Oocytes Using a Hanging Drop Culture System The effects of autologous transfer of biomolecules and cellular components from adult stem cells that overexpress a KIF5B gene to mouse oocytes using a hanging drop method were determined. A KIF5B gene was cloned into an expression vector plasmid and the plasmid was transfected into human adult stem cells.

C57/BL6 mice were primed with PMSG (5 IU/female). The female mice were sacrificed 48 hours later by cervical dislocation. Alcohol was sprayed to the abdominal region of the mice, and an incision was made to expose the abdominal cavity. The ovaries were dissected and diced using a needle. Germinal vesicle (GV) oocytes were selected and were subjected to either control (medium only) or co-culture with adult stem cells. Prior to co-culture, cumulus cells around oocytes were removed using 1 mg/µl hyaluronidase in M2 medium (Sigma-Aldrich, USA). To mimic poor oocyte quality such as the effect of an inhibition of mitochondrial respiratory function, oocytes were treated with 0.05 µM concentration of rotenone for 2 hours. The oocytes were collected after 24 hours of co-culture.

IVM culture medium was prepared using Alpha MEM without amino acids (except glutamine), vitamins and nucleosides. The simplified Alpha MEM containing 10% FBS and 0.2 IU/mL FSH was freshly prepared. Selected oocytes were washed three times in M2 medium and were cultured in a hanging drop composed of 20 µl IVM culture medium with and without 5000 suspended adult stem cells for the treatment group and control group respectively at 37° C. under 5% CO2 in humidified air. After 24 h co-culture, 0.25% trypsin (Life Technologies, USA) was used to detach MSCs on oocytes. Oocytes with polar bodies were recorded as mature oocytes.

Results

KIF5B overexpression in adult stem cells enhanced maturation rate and mitochondrial function of rotenone treated, mitochondrial dysfunctional oocytes by 26.9% and 13.3% respectively (Table 2). Furthermore, KIF5B overexpressing adult stem cells could rescue oocytes by increasing oocyte survival rate by 18.2%. These findings suggested that adult stem cells after KIF5B overexpression had a better improvement effect on mitochondrial dysfunctional oocytes.

TABLE 2

|  | GV(R) + hMSC | GV(R) + hMSC-KIF5B | Improvement |
|---|---|---|---|
| Maturation rate (%) | 4/22 (18.2) | 6/26 (23.1) | +26.9% |
| Survival rate (%) | 22/34 (64.7) | 26/34 (76.5) | +18.2% |
| ATP content (pmol/oocyte) | 1.123 | 1.272 | +13.3% |

Example 3

Effects of Adult Stem Cells on Mouse Oocytes Using a Microfluidic Device of the Invention The effects of a transfer of autologous biomolecules and cellular components from adult stem cells to mouse oocytes using a microfluidic device of the invention were assayed in vitro. Six-week-old C57/BL6 mice were primed with PMSG (5 IU/female). The female mice were sacrificed 48 hours later by cervical dislocation. Alcohol was sprayed to the abdominal region of the mice, and an incision was made to expose the abdominal cavity. The ovaries were dissected and diced using a needle. Germinal vesicle (GV) oocytes were selected and were subjected to either control (medium only) or co-culture with adult stem cells. Prior to co-culture, cumulus cells around oocytes were removed using 85 IU/ml hyaluronidase in M2 medium (Sigma-Aldrich, USA). To mimic poor oocyte quality, such as by inhibiting mitochondrial respiratory function, oocytes were treated with 0.05 µM concentration of rotenone for 2 hours.

Adult stem cells were collected from the adipose tissue prior to in vitro maturation. C57/BL6 mice were sacrificed by cervical dislocation. 5 mg of subcutaneous fat were dissected from the mice. After cutting into small pieces, subcutaneous fat was subjected to type I collagenase (2 mg/mL in PBS, Thermo Fisher Scientific, USA) digestion in 37° C. for one hour. The sample was then centrifuged at 400 g for 15 minutes, and the stromal vascular fraction was collected and cultured on a petri dish in DMEM low glucose medium (Thermo Fisher Scientific, USA) supplemented with 20% fetal bovine serum (Thermo Fisher Scientific, USA) and 1% Penicillin/Streptomycin (Thermo Fisher Scientific, USA) until confluent. Culture medium was changed every 2-3 days.

A microfluidic device of the invention comprising an inlet, a reaction chamber and an outlet was fabricated using SU-8 3025 PDMS polymer. The PDMS polymer was mixed with 10:1 base to curing agent, followed by curing at 60-70° C. Said microfluidic chip was adhered to a cover slip using PDMS polymer of 2:1 base to curing agent, and heated on a heat plate at preferably 170° C.

IVM culture medium was freshly prepared using M2 medium which contains collagen type I (1.5 mg/ml). Selected oocytes were randomized and washed three times in M2 medium prior to use. Adult stem cells were dissociated from a petri dish and counted. 20 µL of IVM culture medium with a concentration of 250 MSCs per µL was prepared and injected into a microfluidic device with an oocyte at a steady pace. The process was observed under a stereomicroscope. Once the oocyte entered the reaction chamber, the injection pace was slowed down. Injection was stopped when the oocyte was surrounded by adult stem cells. The control group consisted of an oocyte cultured in IVM culture medium alone in a microfluidic device.

After being cultured in a microfluidic device for 24 hours or once the oocyte matured to M2 stage, IVM culture medium was injected from the inlet to remove the MSCs from the microfluidic device. Once the MSCs were removed from the microfluidic device, IVM culture medium was injected from the outlet so as to retrieve the oocyte from the inlet. 0.25% trypsin (Life Technologies, cat. no. 25200-056) was used to detach the MSCs if MSCs were attached to the oocyte and could not be removed.

Results

Figure 9A:
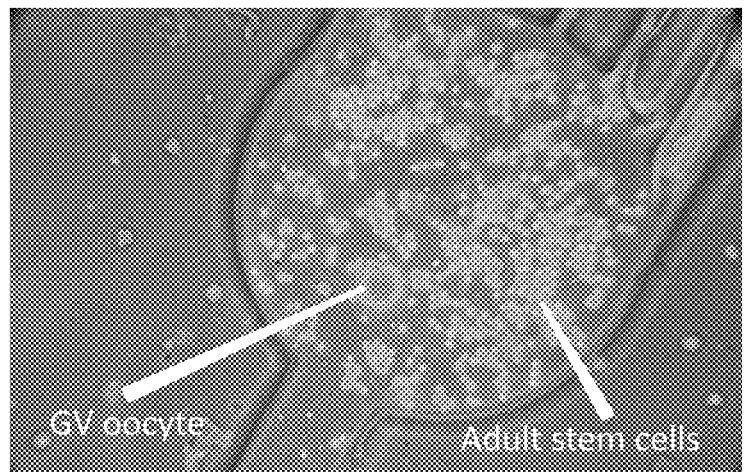
FIG. 9(a) shows a microscopic image taken of a microfluidic tunneling nanotube formation device of the invention immediately after injection of a mouse GV oocyte and adult stem cells
Figure 9B:
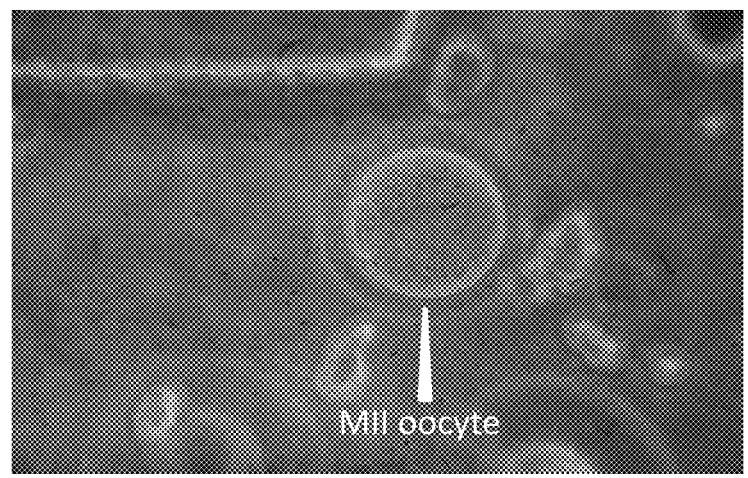
FIG. 9(b) shows a microscopic image showing the successful maturation of mouse MII oocyte after biomolecule and cellular component transfer from mouse adult stem cell (mMSC) through a tunneling nanotube (TNT) in a microfluidic tunneling nanotube formation device of the invention.
Figure 10:
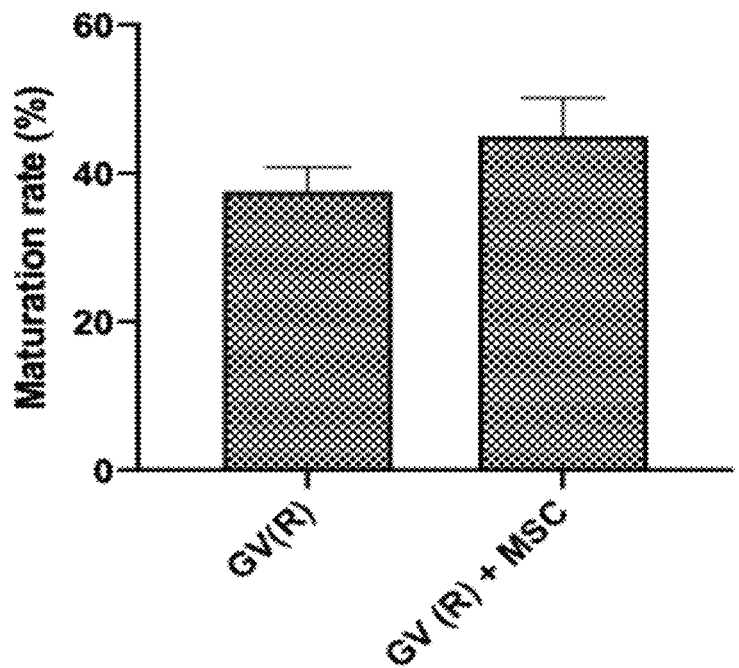
FIG. 10 shows a graph of the improvement in maturation rate before and after biomolecule and cellular component transfer using a microfluidic device of the invention by adult stem cells supplemented with extracellular matrices (GV(R)+MSC).

The microscopic images showed the close proximity between oocyte and adult stem cells, and the successful maturation of oocyte from GV to MII stage (FIG. 9(a) & FIG. 9(b)). The bar chart showed that by using autologous mitochondrial transfer from adult stem cells in a microfluidic device of the invention, the rotenone-treated oocytes showed a 20% increase in maturation rate when compared to IVM culture medium alone in the microfluidic device (FIG. 10).

Example 4

Effects of Menstrual Blood Derived Cells on Oocytes Using a Microfluidic Device of the Invention Menstrual blood was collected from a 25-year old healthy female donor using a menstrual cup. 5 ml menstrual blood was mixed with an equal volume of phosphate-buffered saline (PBS) containing penicillin-streptomycin and 2 mM ethylenediaminetetraacetic acid (EDTA). Menstrual blood mononuclear cells were separated using Ficoll-Hypaque (GE-Healthcare, USA) density-gradient centrifugation. After centrifugation, karyocytes and deciduous endometrium suspending in buffy coat was transferred into new tube and washed two times with PBS. Cells was suspended in DMEM-F12 medium (Thermo Fisher Scientific, USA) supplemented with 20% FBS (Thermo Fisher Scientific, USA). 5,000 cells were used to improve oocyte quality using a hanging drop culture system.

C57/BL6 mice were primed with PMSG (5 IU/female). The female mice were sacrificed 48 hours later by cervical dislocation. Alcohol was sprayed to the abdominal region of the mice, and an incision was made to expose the abdominal cavity. The ovaries were dissected and diced using a needle. Germinal vesicle (GV) oocytes were selected and were subjected to either control (medium only) or co-culture with adult stem cells. Prior to co-culture, cumulus cells around oocytes were removed using 85 IU/ml hyaluronidase in M2 medium (Sigma-Aldrich, USA). To mimic poor oocyte quality such as by inhibiting mitochondrial respiratory function, oocytes were treated with 0.05 µM concentration of rotenone for 2 hours. The oocytes were collected after 24 hours of co-culture.

Results

Figure 11:
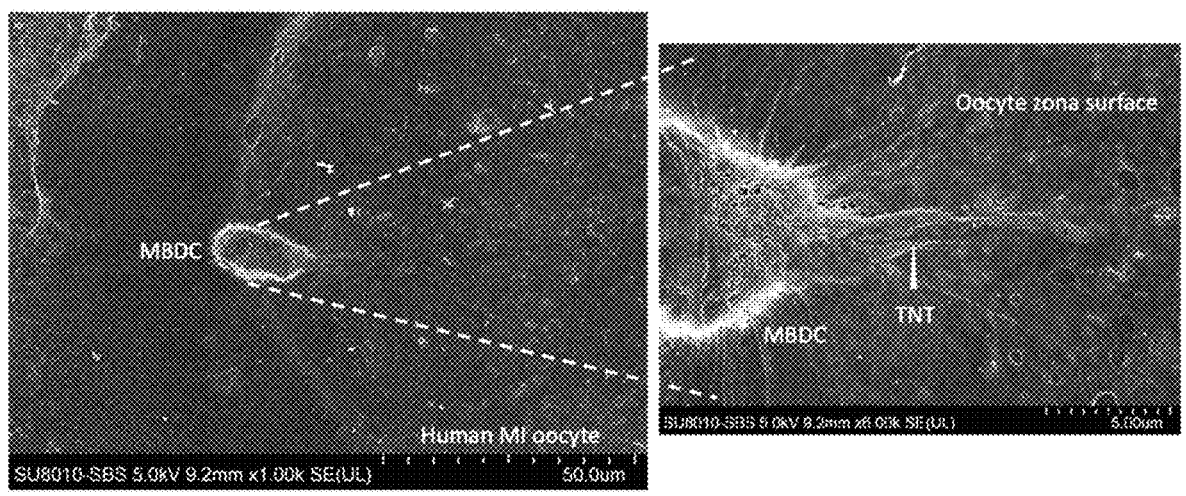
FIG. 11 shows two scanning electron microscopy images of a mouse menstrual blood derived cell (MBDC), a mouse oocyte and the structure of a tunneling nanotube (TNT) in high magnification.
Figure 12:
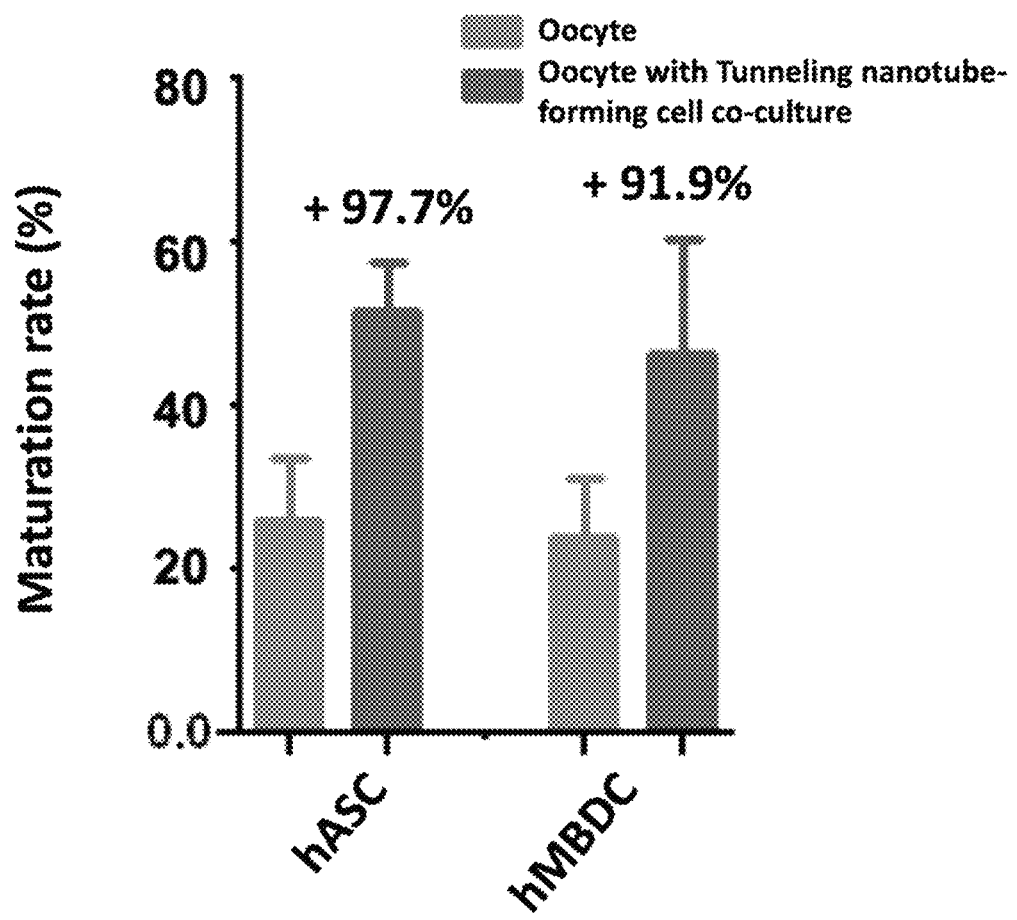
FIG. 12 shows a graph of the improvement in maturation rate of rotenone treated GV with tunneling nanotube forming menstrual blood derived cells (hMBDC) or adult stem cells (hASC).

Scanning electron microscopy confirmed the formation of tunneling nanotubes between menstrual blood derived cells and oocyte (FIG. 11). The data also showed that by using transfer of autologous biomolecules and cellular components from human menstrual blood derived cells (MBDC), the improvement in maturation rate of rotenone-treated oocyte was comparable to adult stem cells (hASC) (FIG. 12).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Asgharzadeh, S., Mirshokraei, P., Hassanpour, H., Ahmadi, E., &. Nazari, H. (2015). The effect of mesenchymal stem cells as co-culture in in vitro nuclear maturation of ovine oocytes. *Animal Science Papers and Reports,* 33(3).
Craven, L., et al., Pronuclear transfer in human embryos to prevent transmission of mitochondrial DNA disease. Nature, 2010. 465(7294): p. 82-5.
Engelstad, K., et al., Attitudes toward prevention of mtDNA-related diseases through oocyte mitochondrial replacement therapy. Hum Reprod, 2016. 31(5): p. 1058-65.
Ling, B., Feng, D. Q., Zhou, Y., Gao, T., Wei, H. M., & Tian, Z. G. (2008). Effect of conditioned medium of mesenchymal stem cells on the in vitro maturation and subsequent development of mouse oocyte. *Brazilian Journal of Medical and Biological Research,* 41(11), 978-985.
Rajabi, Z., Yazdekhasti, H., Mugahi, S. M. H. N., Abbasi, M., Kazemnejad, S., Shirazi, A., . . . & Zarnani, A. H. (2018). Mouse preantral follicle growth in 3D co-culture system using human menstrual blood mesenchymal stem cell. *Reproductive biology,* 18(1), 122-131.
Wang, Z. B., Hao, J. X., Meng, T. G., Guo, L., Dong, M. Z., Fan, L. H., . . . & Yao, Y. Q. (2017). Transfer of autologous mitochondria from adipose tissue-derived stem cells rescues oocyte quality and infertility in aged mice. *Aging* (Albany N.Y.), 9(12), 2480.
Woods, D. C., & Tilly, J. L. (2015, November). Autologous germline mitochondrial energy transfer (AUGMENT) in human assisted reproduction. In *Seminars in reproductive medicine* (Vol. 33, No. 6, p. 410). NIH Public Access.

We claim:

1. A method for generating mature oocytes from immature oocytes, the method comprising:
   culturing one or more immature oocyte in in vitro maturation (IVM) culture medium;
   transfecting one or more tunneling nanotube-forming cell with a vector carrying a microtubule motor protein kinesin family member 5B (KIF5B) gene, thereby causing the overexpression of KIF5B in the one or more tunneling nanotube-forming cell; and
   co-culturing the one or more immature oocyte with at least one of the transfected tunneling nanotube-forming cell under standard culture conditions
   in a manner such that at least one tunneling nanotube-forming cell forms at least one tunneling nanotube to at least one immature oocyte and transfers biomolecules, cellular components, and/or organelles to the at least one immature oocyte through the tunneling nanotube protruded from said at least one tunneling nanotube-forming cell to said at least one immature oocyte for a period of at least one hour.

2. The method of claim 1, wherein said at least one tunneling nanotube-forming cell is an adult stem cell, induced pluripotent stem cell, or menstrual blood derived cell.

3. The method of claim 2, wherein said adult stem cell or induced pluripotent stem cell is isolated from peripheral blood, bone marrow, adipose tissue, dental pulp, umbilical cord blood, or fibroblast or cell populations contained in menstrual blood from the said at least one oocyte.

4. The method of claim 1, wherein said at least one tunneling nanotube-forming cell is autologous to a patient receiving assisted reproductive technology treatment.

5. The method of claim 1, wherein said biomolecules and cellular components comprise one or more nucleic acid, protein, lipid, carbohydrate, or organelle including mitochondria, or any combination thereof.

6. The method of claim 1, wherein said one or more immature oocyte is retrieved during superovulation.

7. The method of claim 1, wherein the IVM culture medium comprises follicle-stimulating hormone (FSH) and serum supplement.

8. The method of claim 1, wherein the IVM culture medium further comprises extracellular matrix components.

9. A method for generating mature oocytes from immature oocytes, the method comprising:
   culturing one or more immature oocyte in IVM culture medium,
   culturing one or more tunneling nanotube-forming cell under standard culture conditions;
   transfecting the one or more tunneling nanotube-forming cell with a vector carrying a microtubule motor protein kinesin family member 5B (KIF5B) gene;
   combining the one or more immature oocyte and the one or more transfected tunneling nanotube-forming cell in a drop of culture medium, and
   suspending said drop of culture medium from an inverted surface, such that said one or more immature oocyte and said one or more tunneling nanotube-forming cell are in close proximity in the hanging drop and at least one tunneling nanotube-forming cell forms at least one tunneling nanotube to at least one immature oocyte and transfers biomolecules, cellular components, and/or organelles to the at least one immature oocyte through the at least one tunneling nanotube protruding from said at least one tunneling nanotube-forming cell for a period of at least one hour.

10. A method for generating mature oocytes from immature oocytes, the method comprising:
culturing one or more immature oocyte in IVM culture medium,
culturing one or more tunneling nanotube-forming cell under standard culture conditions;
transfecting the one or more tunneling nanotube-forming cell with a vector carrying a microtubule motor protein kinesin family member 5B (KIF5B) gene;
injecting said one or more oocyte and said one or more transfected tunneling nanotube-forming cell into a microfluidic device comprising:
a) at least one tunneling nanotube formation chamber;
b) a cell transport network of channels connected to at least one inlet and at least one outlet and the at least one tunneling nanotube formation chamber, wherein the cell transport network of channels is a reservoir for cells and cell culture medium and controls the flow rate of the cells and the culture medium through the device, and
c) a constriction comprising one or more microchannels having a diameter distinct from the diameter of the channels of the cell transport network; and
co-culturing the one or more immature oocyte with the one or more transfected tunneling nanotube-forming cell in the microfluidic device in a manner such that at least one tunneling nanotube-forming cell forms at least one tunneling nanotube to at least one immature oocyte and transfers biomolecules, cellular components, and/or organelles to the at least one immature oocyte through the tunneling nanotube protruded from said at least one tunneling nanotube-forming cell to said at least one immature oocyte for a period of at least one hour.

* * * * *